(12) United States Patent
Weitzner et al.

(10) Patent No.: US 12,390,269 B2
(45) Date of Patent: *Aug. 19, 2025

(54) SPHINCTEROTOMES AND METHODS FOR USING SPHINCTEROTOMES

(71) Applicant: BOSTON SCIENTIFIC SCIMED, INC., Maple Grove, MN (US)

(72) Inventors: Barry Weitzner, Acton, MA (US); Paul Smith, Smithfield, RI (US); Peter L. Dayton, Brookline, MA (US); Evan Wilder, Boston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 290 days.

This patent is subject to a terminal disclaimer.

(21) Appl. No.: 18/074,839

(22) Filed: Dec. 5, 2022

(65) Prior Publication Data

US 2023/0097615 A1 Mar. 30, 2023

Related U.S. Application Data

(63) Continuation of application No. 16/436,598, filed on Jun. 10, 2019, now Pat. No. 11,517,371.
(Continued)

(51) Int. Cl.
*A61B 18/14* (2006.01)
*A61B 17/22* (2006.01)
(Continued)

(52) U.S. Cl.
CPC ...... *A61B 18/149* (2013.01); *A61B 17/32056* (2013.01); *A61B 18/1206* (2013.01);
(Continued)

(58) Field of Classification Search
CPC ...... A61B 2018/1407; A61B 2018/141; A61B 2018/144
See application file for complete search history.

(56) References Cited

U.S. PATENT DOCUMENTS

| 4,553,545 A | 11/1985 | Maass et al. |
| 4,776,337 A | 10/1988 | Palmaz |

(Continued)

FOREIGN PATENT DOCUMENTS

| CN | 203183028 U | 9/2013 |
| EP | 3115014 A1 | 1/2017 |

(Continued)

OTHER PUBLICATIONS

International Search Report from PCT/2014/020086 dated Jun. 24, 2014.
(Continued)

*Primary Examiner* — Ronald Hupczey, Jr.
(74) *Attorney, Agent, or Firm* — Seager, Tufte & Wickhem, LLP

(57) ABSTRACT

Sphincterotomes and methods for making and using sphincterotomes are disclosed. An example sphincterotome may include an elongate shaft having an outer surface and a distal end region. The sphincterotome may also include a sphincterotome wire assembly having a distal end coupled to the distal end region of the elongate shaft and a body portion extending along the outer surface of the elongate shaft. The sphincterotome wire assembly may be designed to shift the distal end region of the elongate shaft between a first configuration and a curved configuration. The body portion of the sphincterotome wire assembly may include a cutting region and a non-conductive region.

20 Claims, 57 Drawing Sheets

Related U.S. Application Data

(60) Provisional application No. 62/768,432, filed on Nov. 16, 2018, provisional application No. 62/683,318, filed on Jun. 11, 2018.

(51) Int. Cl.
*A61B 17/3205* (2006.01)
*A61B 18/00* (2006.01)
*A61B 18/12* (2006.01)
*A61B 90/00* (2016.01)

(52) U.S. Cl.
CPC .......... *A61B 18/1492* (2013.01); *A61B 90/39* (2016.02); *A61B 2017/22038* (2013.01); *A61B 2018/00553* (2013.01); *A61B 2018/00601* (2013.01); *A61B 2018/126* (2013.01); *A61B 2018/144* (2013.01); *A61M 2205/32* (2013.01)

(56) References Cited

U.S. PATENT DOCUMENTS

| | | |
|---|---|---|
| 5,064,435 A | 11/1991 | Porter |
| 5,415,656 A | 5/1995 | Tihon et al. |
| 5,425,765 A | 6/1995 | Tiefenbrun et al. |
| 5,445,646 A | 8/1995 | Euteneuer et al. |
| 5,824,046 A | 10/1998 | Smith et al. |
| 6,042,605 A | 3/2000 | Martin et al. |
| 6,050,995 A | 4/2000 | Durgin |
| 6,099,559 A | 8/2000 | Nolting |
| 6,099,561 A | 8/2000 | Alt |
| 6,120,536 A | 9/2000 | Ding et al. |
| 6,139,573 A | 10/2000 | Sogard et al. |
| 6,143,022 A | 11/2000 | Shull et al. |
| 6,156,064 A | 12/2000 | Chouinard |
| 6,159,239 A | 12/2000 | Greenhalgh |
| 6,162,244 A | 12/2000 | Braun et al. |
| 6,165,211 A | 12/2000 | Thompson |
| 6,168,619 B1 | 1/2001 | Dinh et al. |
| 6,254,627 B1 | 7/2001 | Freidberg |
| 6,315,794 B1 | 11/2001 | Richter |
| 6,319,278 B1 | 11/2001 | Quinn |
| 6,334,867 B1 | 1/2002 | Anson |
| 6,352,553 B1 | 3/2002 | Van Der Burg et al. |
| 6,364,904 B1 | 4/2002 | Smith |
| 6,645,242 B1 | 11/2003 | Quinn |
| 6,712,817 B1 * | 3/2004 | Goto ................. A61B 18/1485 606/47 |
| 6,790,225 B1 | 9/2004 | Shannon et al. |
| 7,118,592 B1 | 10/2006 | Dang et al. |
| 7,425,219 B2 | 9/2008 | Quadri |
| 7,645,298 B2 | 1/2010 | Hartley et al. |
| 7,828,837 B2 | 11/2010 | Khoury |
| 8,142,431 B2 | 3/2012 | Ducharme |
| 8,147,538 B2 | 4/2012 | Brown et al. |
| 8,167,926 B2 | 5/2012 | Hartley et al. |
| 8,231,665 B2 | 7/2012 | Kim et al. |
| 8,317,854 B1 | 11/2012 | Ryan et al. |
| 9,056,001 B2 | 6/2015 | Armstrong et al. |
| 10,154,917 B2 | 12/2018 | Bogert |
| 10,405,966 B2 | 9/2019 | Johnson |
| 11,517,371 B2 * | 12/2022 | Weitzner ................ A61B 90/39 |
| 2001/0021870 A1 | 9/2001 | Edwin et al. |
| 2001/0032009 A1 | 10/2001 | Layne et al. |
| 2001/0039446 A1 | 11/2001 | Edwin et al. |
| 2002/0002397 A1 | 1/2002 | Martin et al. |
| 2003/0199967 A1 | 10/2003 | Hartley et al. |
| 2004/0054397 A1 | 3/2004 | Smith et al. |
| 2004/0087886 A1 | 5/2004 | Gellman |
| 2005/0059923 A1 | 3/2005 | Gamboa |
| 2007/0032857 A1 | 2/2007 | Schmid et al. |
| 2007/0142904 A1 | 6/2007 | Sorenson et al. |
| 2007/0219612 A1 | 9/2007 | Andreas et al. |
| 2007/0282358 A1 | 12/2007 | Remiszewski et al. |
| 2008/0140176 A1 | 6/2008 | Krause et al. |
| 2010/0100170 A1 | 4/2010 | Tan et al. |
| 2011/0022154 A1 | 1/2011 | Hamer et al. |
| 2012/0130472 A1 | 5/2012 | Shaw |
| 2012/0193018 A1 | 8/2012 | Banas et al. |
| 2012/0239134 A1 | 9/2012 | Dierking |
| 2012/0296406 A1 | 11/2012 | Minion |
| 2013/0204343 A1 | 8/2013 | Shalev |
| 2013/0261731 A1 | 10/2013 | Zhou et al. |
| 2013/0274851 A1 | 10/2013 | Kelly |
| 2014/0276808 A1 | 9/2014 | Gittard et al. |
| 2015/0223925 A1 | 8/2015 | Rasmussen et al. |
| 2016/0058585 A1 | 3/2016 | Seddon et al. |
| 2019/0151072 A1 | 5/2019 | Walzman |

FOREIGN PATENT DOCUMENTS

| | | |
|---|---|---|
| JP | 1996509894 A | 10/1996 |
| JP | 2000237202 A | 9/2000 |
| JP | 2000279532 A | 10/2000 |
| JP | 2010531712 A | 9/2010 |
| WO | 9600103 A1 | 1/1996 |
| WO | 1998008456 A1 | 3/1998 |
| WO | 9915105 A1 | 4/1999 |
| WO | 2001001886 A1 | 1/2001 |
| WO | 2009145901 A1 | 12/2009 |
| WO | 2011076408 A1 | 6/2011 |
| WO | 2013123147 A1 | 8/2013 |
| WO | 2014107748 A2 | 7/2014 |

OTHER PUBLICATIONS

International Search Report and Written Opinion dated Sep. 19, 2019 for International Application No. PCT/US2019/036390.
International Search Report and Written Opinion dated Dec. 3, 2021 for International Application No. PCT/US2021/048178.

* cited by examiner

SPHINCTEROTOMES AND METHODS FOR USING SPHINCTEROTOMES

CROSS-REFERENCE TO RELATED APPLICATIONS

This application is a continuation of U.S. patent Ser. No. 16/436,598, filed Jun. 10, 2019, now U.S. Pat. No. 11,517,371; which claims the benefit of priority of U.S. Provisional Application Ser. No. 62/768,432, filed Nov. 16, 2018 and U.S. Provisional Application Ser. No. 62/683,318 filed Jun. 11, 2018, the entirety of which are incorporated herein by reference.

TECHNICAL FIELD

The present disclosure pertains to medical devices, and methods for manufacturing medical devices. More particularly, the present disclosure pertains to sphincterotomes.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A sphincterotome is disclosed. The sphincterotome comprises: an elongate shaft having an outer surface and a distal end region; a sphincterotome wire assembly having a distal end coupled to the distal end region of the elongate shaft and a body portion extending along the outer surface of the elongate shaft; wherein the sphincterotome wire assembly is designed to shift the distal end region of the elongate shaft between a first configuration and a curved configuration; and wherein the body portion of the sphincterotome wire assembly includes a cutting region and a non-conductive region.

Alternatively or additionally to any of the embodiments above, the cutting region of the sphincterotome wire assembly is defined by a conductive cutting wire.

Alternatively or additionally to any of the embodiments above, the non-conductive region of the sphincterotome wire assembly includes a non-conductive wire coupled to the conductive cutting wire.

Alternatively or additionally to any of the embodiments above, the non-conductive wire is coupled to the conductive cutting wire by a housing.

Alternatively or additionally to any of the embodiments above, the elongate shaft includes a distal anchor, wherein the distal end of the sphincterotome wire assembly is coupled to the distal end region of the elongate shaft at the distal anchor, and wherein the sphincterotome wire assembly includes a proximal region that extends through a port formed along the elongate shaft and into a lumen formed in the elongate shaft.

Alternatively or additionally to any of the embodiments above, the elongate shaft includes a proximal anchor, wherein the conductive cutting wire has a proximal end region coupled to the distal end region of the elongate shaft at the proximal anchor, and wherein the proximal anchor is disposed between the distal anchor and the port.

Alternatively or additionally to any of the embodiments above, the elongate shaft includes a distal port, and wherein the conductive cutting wire extends through the distal port and extends proximally within a lumen formed in the elongate shaft.

Alternatively or additionally to any of the embodiments above, the conductive cutting wire includes a conductive coating.

Alternatively or additionally to any of the embodiments above, the conductive cutting wire includes a cutting wire and a ground wire.

Alternatively or additionally to any of the embodiments above, the non-conductive region of the body portion of the sphincterotome wire assembly includes an insulating member coupled thereto.

Alternatively or additionally to any of the embodiments above, the elongate shaft includes an insulating projection and wherein the non-conductive region of the body portion of the sphincterotome wire assembly is coupled to the insulating projection.

Alternatively or additionally to any of the embodiments above, the insulating projection includes one or more of a flap, an opening, and a groove formed therein.

A sphincterotome is disclosed. The sphincterotome comprises: an elongate shaft having an outer surface, a distal end region, and a distal anchor disposed along the distal end region; a cutting wire coupled to the distal anchor and having a cutting region extending along the outer surface of the elongate shaft; a non-conductive cord coupled to the cutting region of the cutting wire and extending proximally therefrom; wherein the cutting wire, the non-conductive cord, or both are designed to shift the distal end region of the elongate shaft between a first configuration and a curved configuration.

Alternatively or additionally to any of the embodiments above, the non-conductive cord extends through a port formed in the elongate shaft and into a lumen formed in the elongate shaft.

Alternatively or additionally to any of the embodiments above, the cutting wire is coupled to the elongate shaft at a medial anchor, the medial anchor being disposed between the distal anchor and the port.

Alternatively or additionally to any of the embodiments above, the non-conductive cord is coupled to the cutting region of the cutting wire at a non-conductive housing.

Alternatively or additionally to any of the embodiments above, further comprising a ground wire coupled to the cutting wire.

A sphincterotome is disclosed. The sphincterotome comprises: an elongate shaft having a distal anchor, a projection formed in the elongate shaft and disposed proximally of the distal anchor; a cutting wire having a distal end coupled to the distal anchor and a proximal region coupled to the projection; wherein the cutting wire is designed to shift the elongate shaft between a first configuration and a curved configuration; and wherein when the elongate shaft is in the curved configuration, at least a portion of the projection is radially spaced from an outer surface of the elongate shaft.

Alternatively or additionally to any of the embodiments above, the projection includes an insulating material.

Alternatively or additionally to any of the embodiments above, the projection has a channel formed therein.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
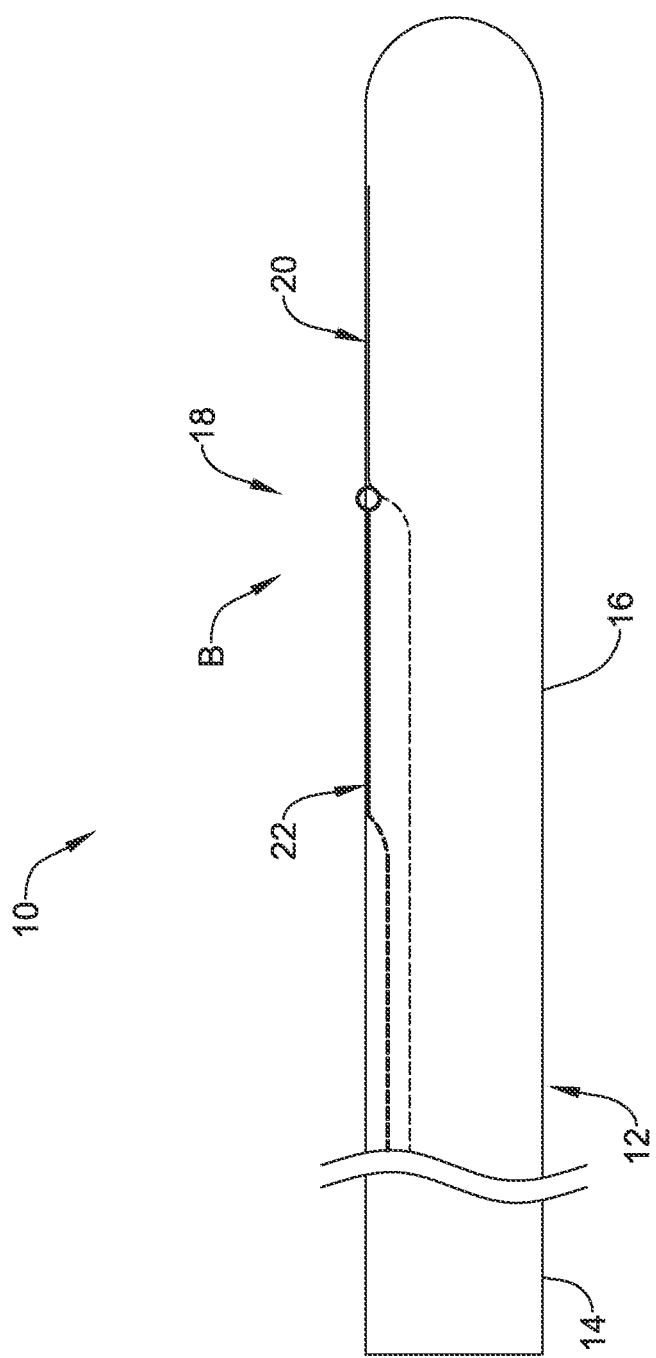
FIGS. 1-2 are side views of a portion of an example sphincterotome.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Endoscopic retrograde cholangiopancreatography (ERCP) may be utilized to diagnose and treat various disorders of the pancreaticobiliary system. A clinician may use a sphincterotome to cannulate the papillary orifice. The sphincterotome may have a number of features including a cutting wire for performing a sphincterotomy. When performing sphincterotomy, the distal portion of the cutting wire may be used for cutting tissue. The proximal portion of the wire, in general, may not serve a cutting function. Additionally, while performing sphincterotomy, the folds of the duodenal wall may come in contact with the proximal portion of the cutting wire, which could result in an ancillary tissue burn. Disclosed herein are sphincterotomes where the proximal portion of the cutting wire is designed to be non-conductive, insulated, and/or otherwise non-cutting.

Figure 2:
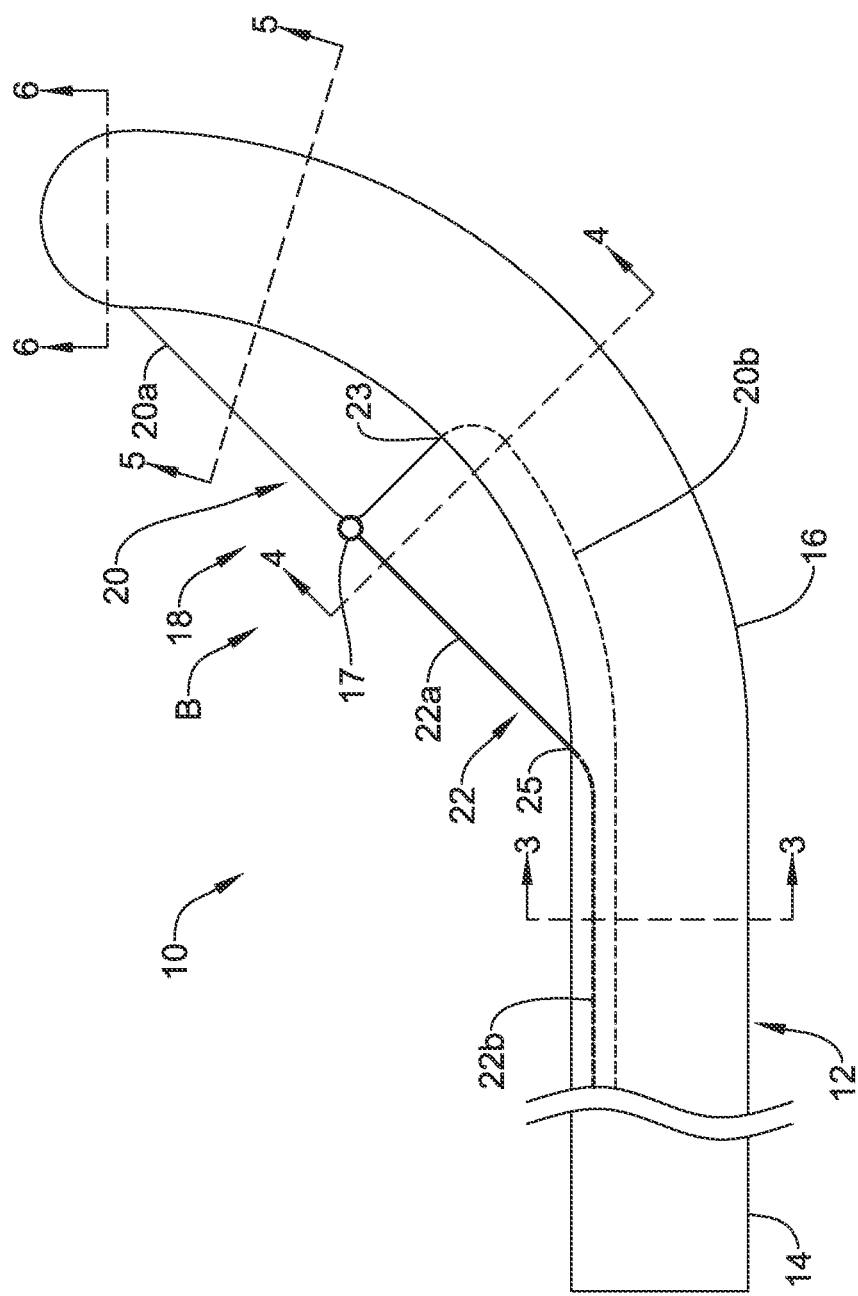

FIGS. 1-2 illustrates an example sphincterotome 10. The sphincterotome 10 may include an elongate shaft 12 having a proximal end region 14 and a distal end region 16. The sphincterotome 10 may include a sphincterotome wire assembly 18. The sphincterotome wire assembly 18 may be designed to shift the distal end region 16 of the elongate shaft 12 between a first configuration (e.g., as depicted in FIG. 1) and a curved or bowed configuration (e.g., as depicted in FIG. 2). For example, exerting a proximal force on one or more of the components of the sphincterotome wire assembly 18 may cause the elongate shaft 12 to shift between configurations.

The sphincterotome wire assembly 18 may include a body portion B generally defined as the portion of the sphincterotome wire assembly 18 extending along the outer surface of the elongate shaft 12 and that may be described as extending diagonally akin to the string of a bow when the elongate shaft 12 is in the curved configuration (e.g., as depicted in FIG. 2).

Figure 3:
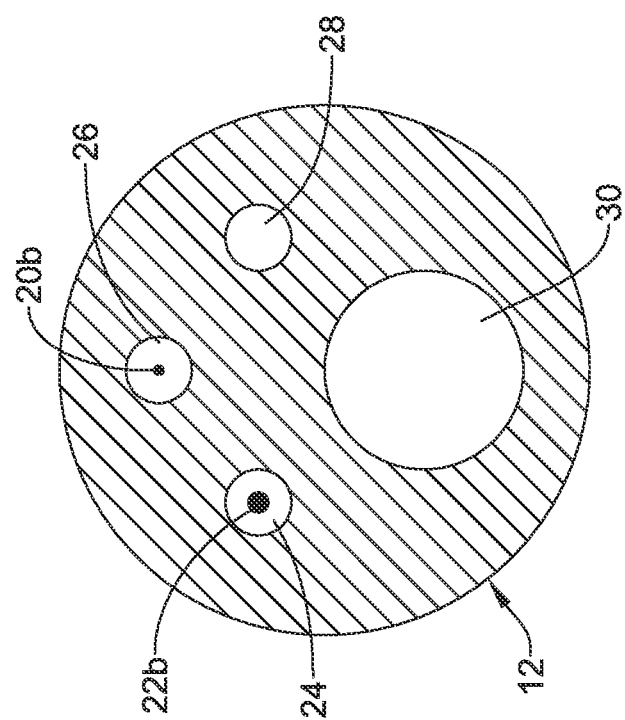
FIGS. 3-6 are cross-sectional views of the sphincterotome shown in FIGS. 1-2.
Figure 4:
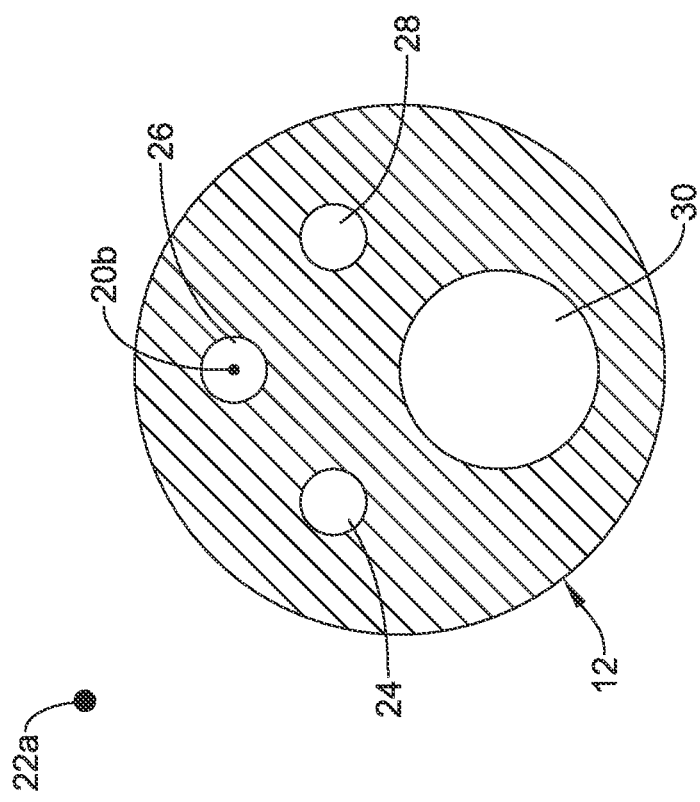
Figure 5:
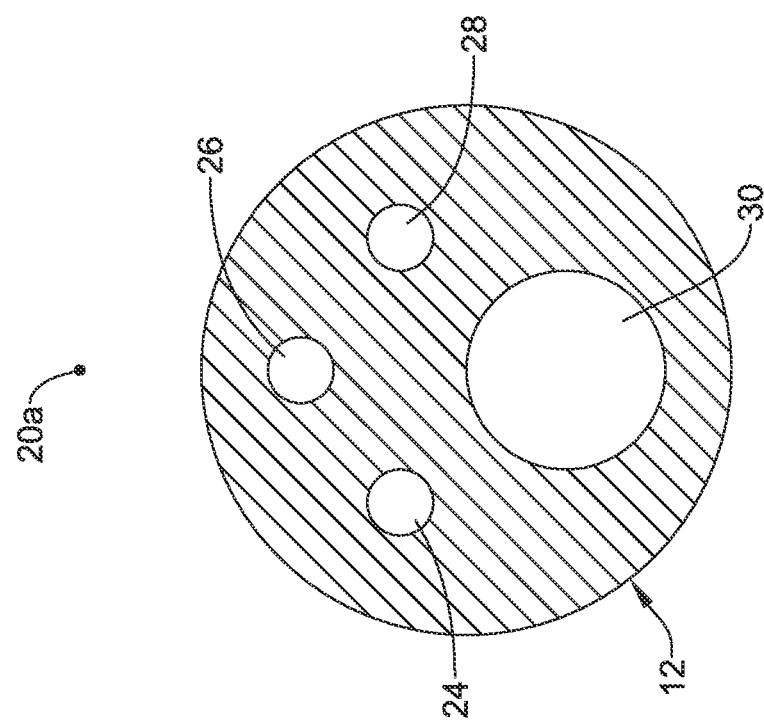
Figure 6:
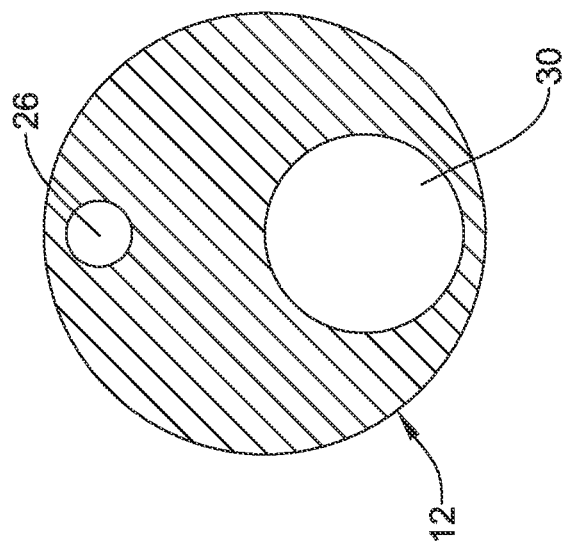

The sphincterotome wire assembly 18 may include a first member or portion 20 and a second member or portion 22. The first member 20 may be coupled to the second member 22 at a joint 17. In this example, the first member 20 may take the form of a wire having a cutting region 20a and a proximally-extending region 20b. A distal end region of the first member 20 may be anchored to the distal end region 16 of the shaft 12 (e.g., using, for example, a metallic anchor). A portion of the cutting region 20a of the first member 20 may be secured to or otherwise extend through a loop or opening defined at the joint 17 and then the first member 20 may extend generally toward the outer surface of the shaft 12. In some instances, the first member 20 may extend through a first port 23 formed in the shaft 12 and into a lumen of the shaft 12 (e.g., the second lumen 26 as shown, for example, in FIG. 3). The second member 22 may take the form of a wire or non-conductive cord (e.g., formed form a non-conductive material such as aramid) having a non-conductive region 22a and a proximally-extending region 22b. In some instances, a distal end region of the second member 22 may be secured to the joint 17. The second member 22 may extend through a second port 25 formed in the shaft 12 and into a lumen of the shaft 12 (e.g., the first lumen 24 as shown, for example, in FIG. 3). In at least some instances, the first port 23 may be disposed along the shaft 12 at a position between the location where the distal end region of the first member 20 is anchored to the shaft 12 and the second port 25. In other words, the first port 23 may be disposed between the distal anchor and the second port 25.

The body portion B of the sphincterotome wire assembly 18 may include the cutting region 20a of the first member 20 and the non-conductive region 22a of the second member 22. In at least some instances, the first member 20 is a conductive wire (e.g., an RF conductive wire) that can be energized. When doing so, the cutting region 20a may be energized so as to facilitate cutting. In contrast, the second member 22 may be non-conductive. Accordingly, the non-conductive region 22a may generally be described as being non-energized, non-cutting, and/or otherwise designed so as to not facilitate cutting.

FIGS. 3-6 are cross-sectional views taken at various locations along the shaft 12. Here it can be seen that the shaft 12 may include a number of different lumens. For example, the shaft 12 may include a first lumen 24, a second lumen 26, a third lumen 28, and a fourth lumen 30. In this example, the proximally-extending region 22b of the second member 22 may extend through the first lumen 24. The proximally-extending region 20b of the first member 20 may extend through the second lumen 26. The third lumen 28 may be used for infusing a fluid such as a contrast media. The fourth lumen 30 may be a guidewire lumen.

Figure 7:
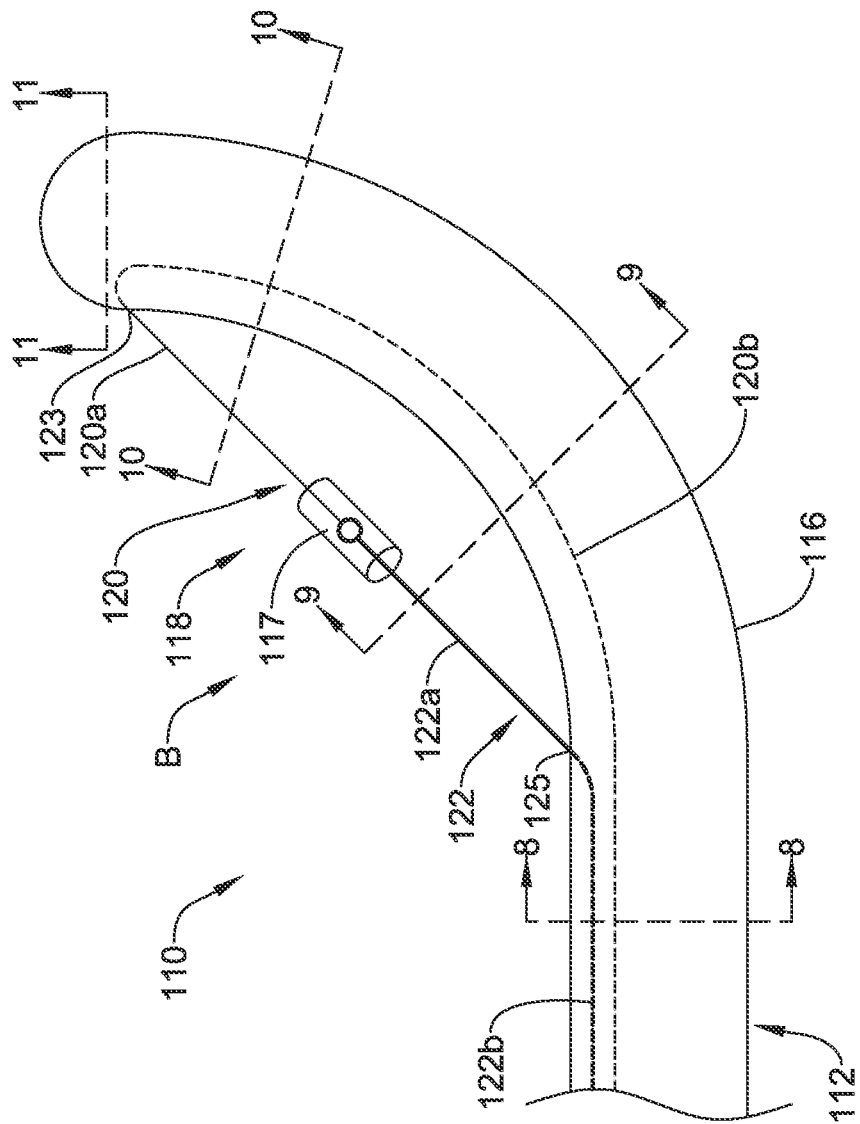
FIG. 7 is a side view of a portion of an example sphincterotome.

FIG. 7 illustrates another example sphincterotome 110 that may be similar in form and function to other sphincterotomes disclosed herein. The sphincterotome 110 includes a shaft 112 having a distal end region 116. The sphincterotome 110 may include a sphincterotome wire assembly 118. The sphincterotome wire assembly 118 may be designed to shift the distal end region 116 of the elongate shaft 112 between a first configuration and a curved or bowed configuration.

Figure 8:
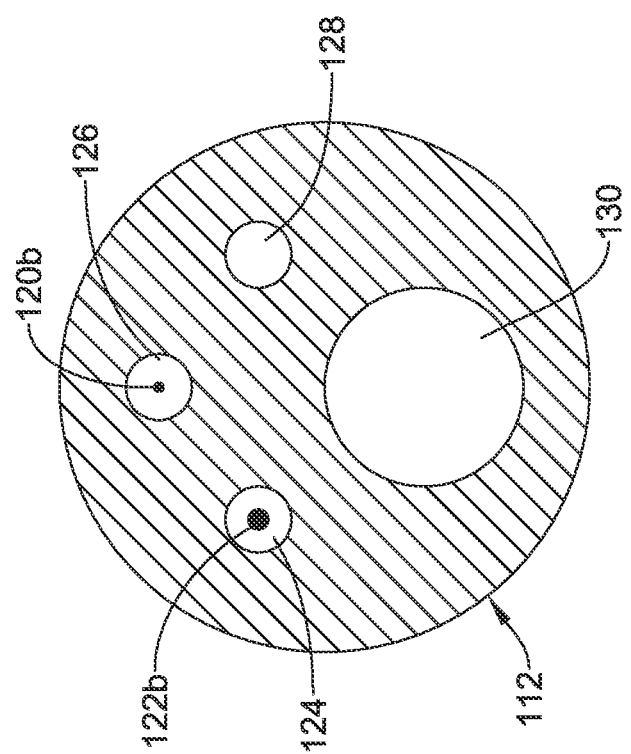
FIGS. 8-11 are cross-sectional views of the sphincterotome shown in FIG. 7.
Figure 9:
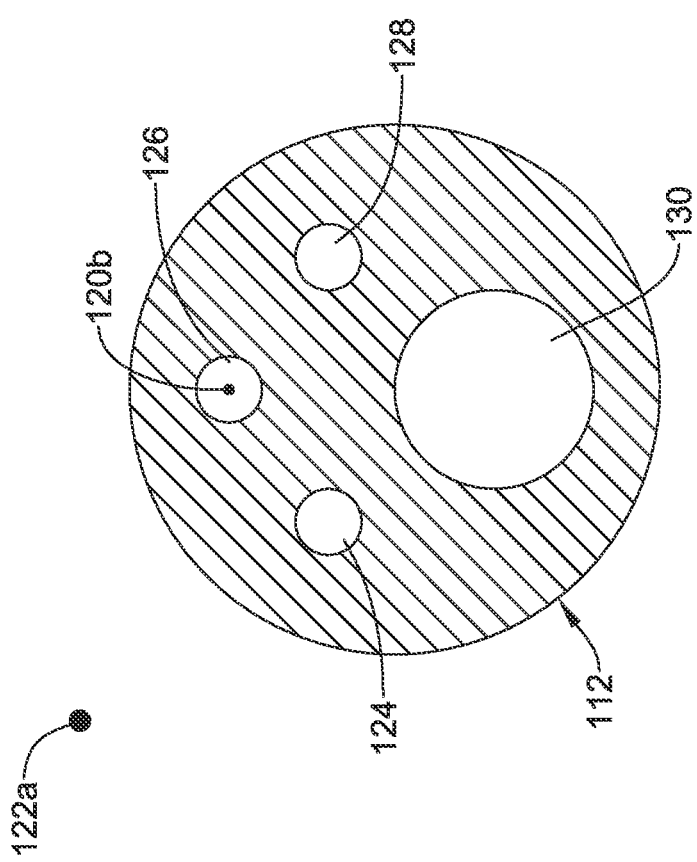
Figure 10:
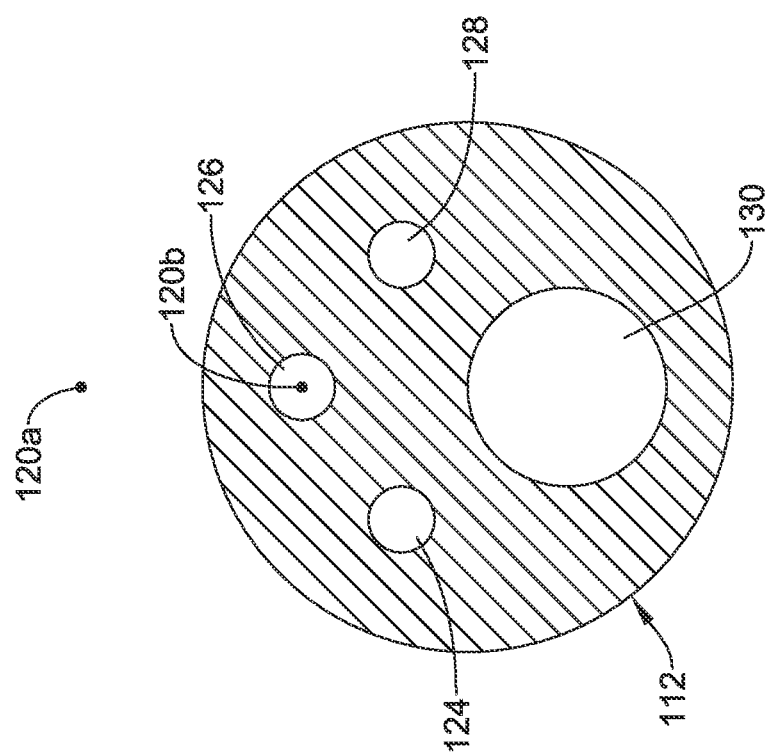
Figure 11:
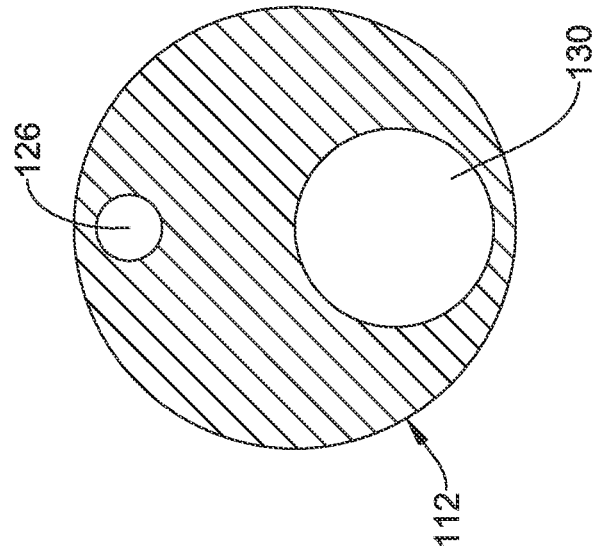

The sphincterotome wire assembly 118 may include a body portion B generally defined as the portion of the sphincterotome wire assembly 118 extending along the outer surface of the elongate shaft 112 and that may be described as extending diagonally akin to the string of a bow when the elongate shaft 112 is in the curved configuration. The sphincterotome wire assembly 118 may include a first member or portion 120 and a second member or portion 122. The first member 120 may be coupled to the second member 122 at a joint 117. In this example, the joint 117 may take the form of a non-conductive housing designed to be secured to both the first member 120 and the second member 122. This may include a mechanical or other type of connection. The first member 120 may take the form of a wire having a cutting region 120a and a proximally-extending region 120b. A distal end region of the first member 120 may extend through a first port 123 formed in the shaft 112 and into a lumen of the shaft 112 (e.g., the second lumen 126 as shown, for example, in FIG. 8). The second member 122 may take the form of a wire or non-conductive cord having a non-conductive region 122a and a proximally-extending region 122b. The second member 122 may extend through a second port 125 formed in the shaft 112 and into a lumen of the shaft 112 (e.g., the first lumen 124 as shown, for example, in FIG. 8).

The body portion B of the sphincterotome wire assembly 118 may include the cutting region 120a of the first member 120 and the non-conductive region 122a of the second member 122. In at least some instances, the first member 120 is a conductive wire (e.g., an RF conductive wire) that can be energized. When doing so, the cutting region 120a may be energized so as to facilitate cutting. In contrast, the second member 122 may be non-conductive. Accordingly, the non-conductive region 122a may generally be described as being non-energized, non-cutting, and/or otherwise designed so as to not facilitate cutting.

FIGS. 8-11 are cross-sectional views taken at various locations along the shaft 112. Here it can be seen that the shaft 112 may include a number of different lumens. For example, the shaft 112 may include a first lumen 124, a second lumen 126, a third lumen 128, and a fourth lumen 130. In this example, the proximally-extending region 122b of the second member 122 may extend through the first lumen 124. The proximally-extending region 120b of the first member 120 may extend through the second lumen 126. The third lumen 128 may be used for infusing a fluid such as a contrast media. The fourth lumen 130 may be a guidewire lumen.

Figure 12:
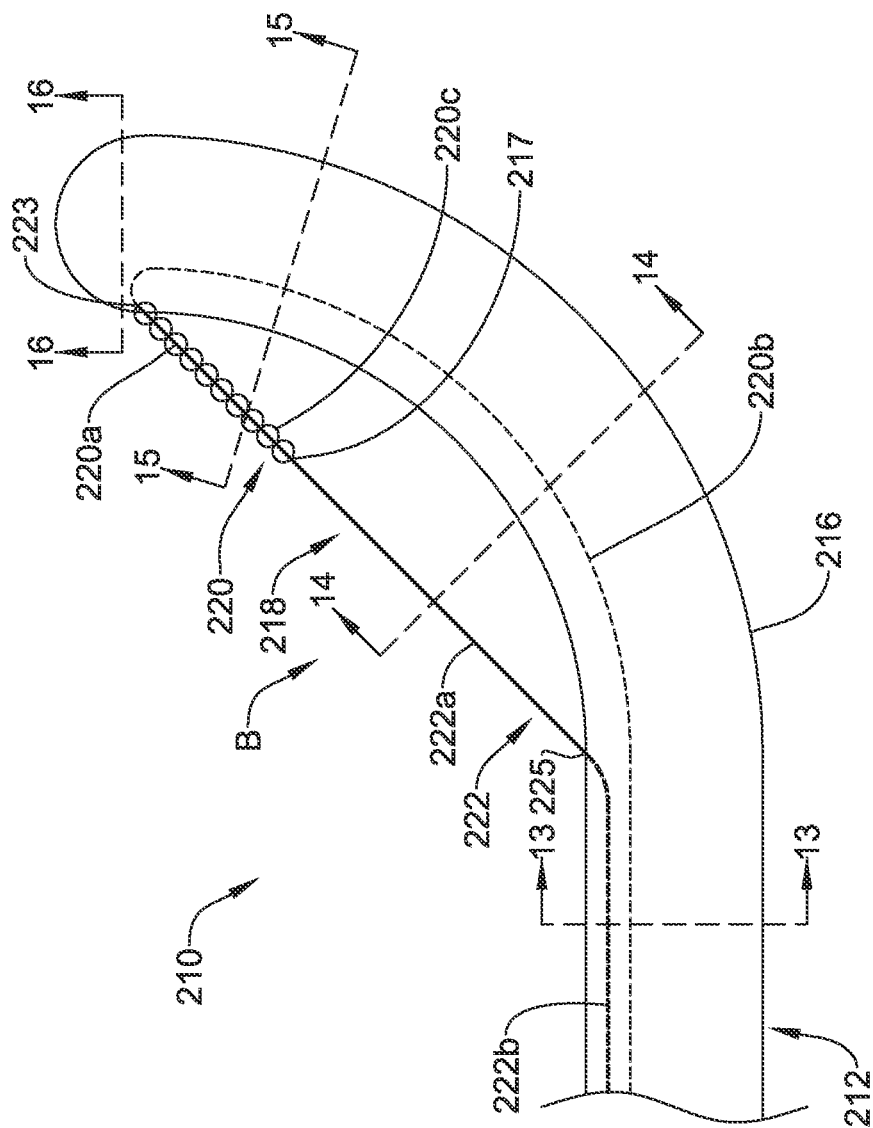
FIG. 12 is a side view of a portion of an example sphincterotome.

FIG. 12 illustrates another example sphincterotome 210 that may be similar in form and function to other sphincterotomes disclosed herein. The sphincterotome 210 includes a shaft 212 having a distal end region 216. The sphincterotome 210 may include a sphincterotome wire assembly 218. The sphincterotome wire assembly 218 may be designed to shift the distal end region 216 of the elongate shaft 212 between a first configuration and a curved or bowed configuration.

Figure 13:
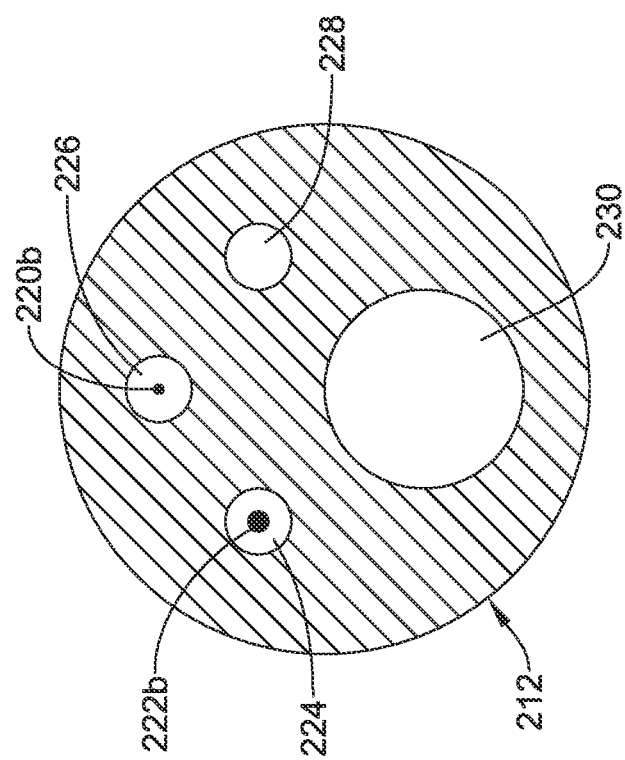
FIGS. 13-16 are cross-sectional views of the sphincterotome shown in FIG. 12.
Figure 14:
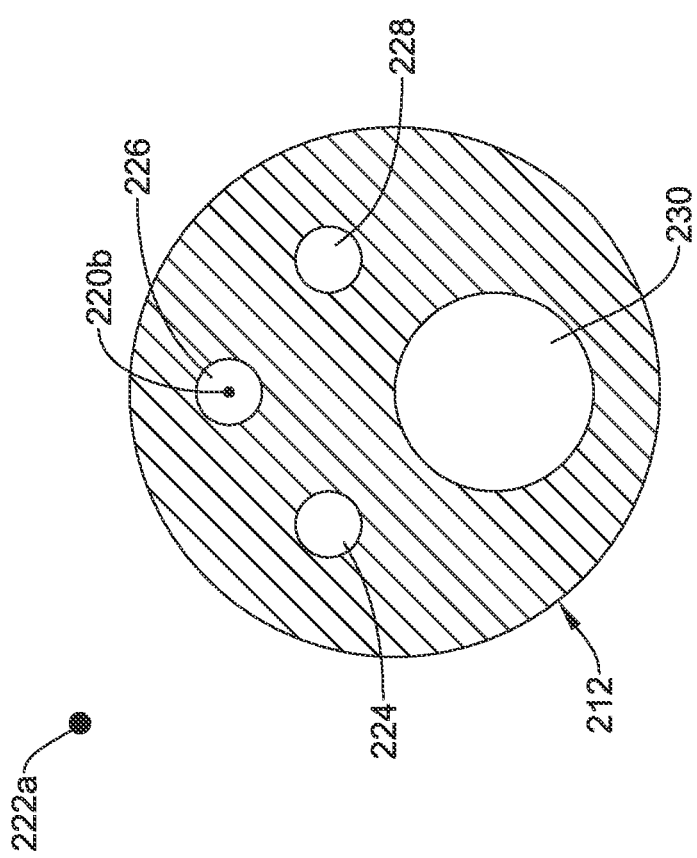
Figure 15:
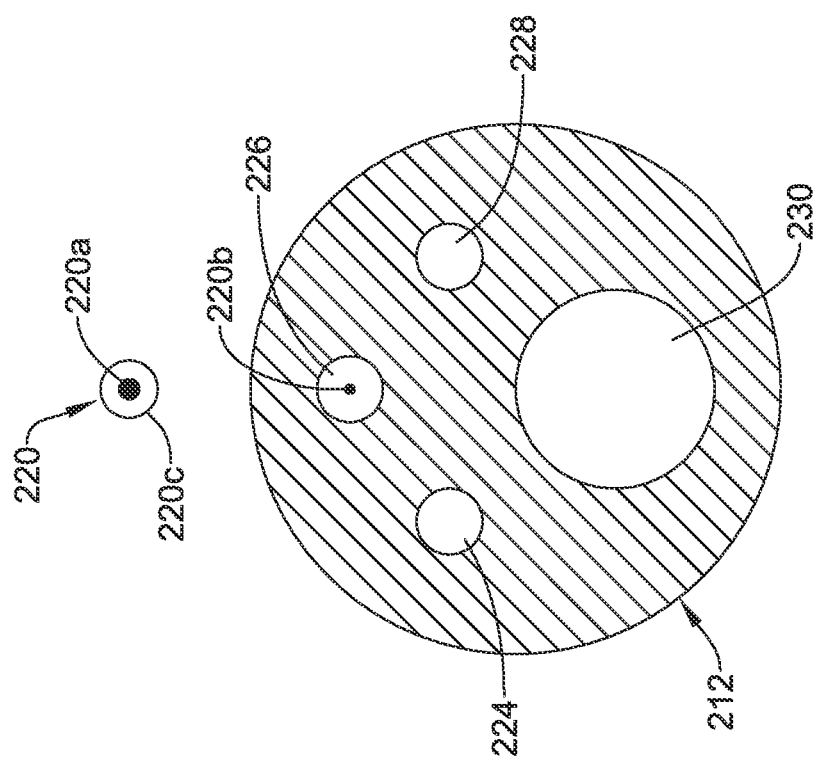
Figure 16:
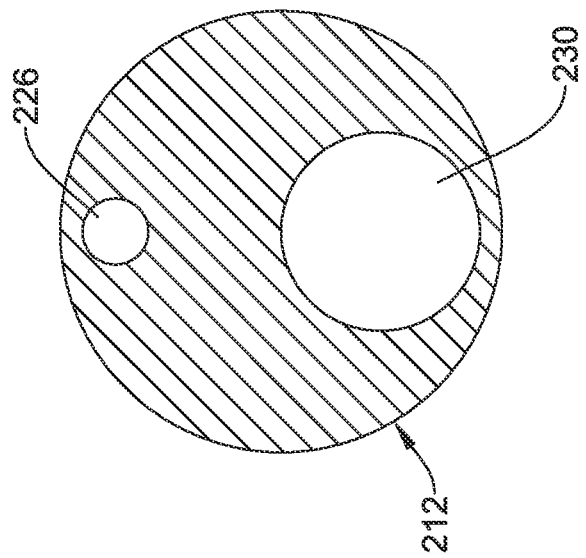

The sphincterotome wire assembly 218 may include a body portion B generally defined as the portion of the sphincterotome wire assembly 218 extending along the outer surface of the elongate shaft 212 and that may be described as extending diagonally akin to the string of a bow when the elongate shaft 212 is in the curved configuration. The sphincterotome wire assembly 218 may include a first member or portion 220 and a second member or portion 222. The first member 220 may be coupled to the second member 222 at a joint 217. The first member 220 may take the form of a wire having a cutting region 220a and a proximally-extending region 220b. A distal end region of the first member 220 may extend through a first port 223 formed in the shaft 212 and into a lumen of the shaft 212 (e.g., the second lumen 226 as shown, for example, in FIG. 13). The second member 222 may take the form of a wire or non-conductive cord having a non-conductive region 222a and a proximally-extending region 222b. The second member 222 may extend through a second port 225 formed in the shaft 212 and into a lumen of the shaft 212 (e.g., the first lumen 224 as shown, for example, in FIG. 13).

The body portion B of the sphincterotome wire assembly 218 may include the cutting region 220a of the first member 220 and the non-conductive region 222a of the second member 222. In at least some instances, the first member 220 is a wire having a conductive member 220c that can be energized. In some instances, the conductive member 220c takes the form of a conductive coating, a conductive paint, a conductive coil (e.g., surrounding the cutting region 220a), and/or the like. The cutting region 220a may be energized so as to facilitate cutting. In contrast, the second member 222 may be non-conductive. Accordingly, the non-conductive region 222a may generally be described as being non-energized, non-cutting, and/or otherwise designed so as to not facilitate cutting.

FIGS. 13-16 are cross-sectional views taken at various locations along the shaft 212. Here it can be seen that the shaft 212 may include a number of different lumens. For example, the shaft 212 may include a first lumen 224, a second lumen 226, a third lumen 228, and a fourth lumen 230. In this example, the proximally-extending region 222b of the second member 222 may extend through the first lumen 224. The proximally-extending region 220b of the first member 220 may extend through the second lumen 226. The third lumen 228 may be used for infusing a fluid such as a contrast media. The fourth lumen 230 may be a guidewire lumen.

Figure 17:
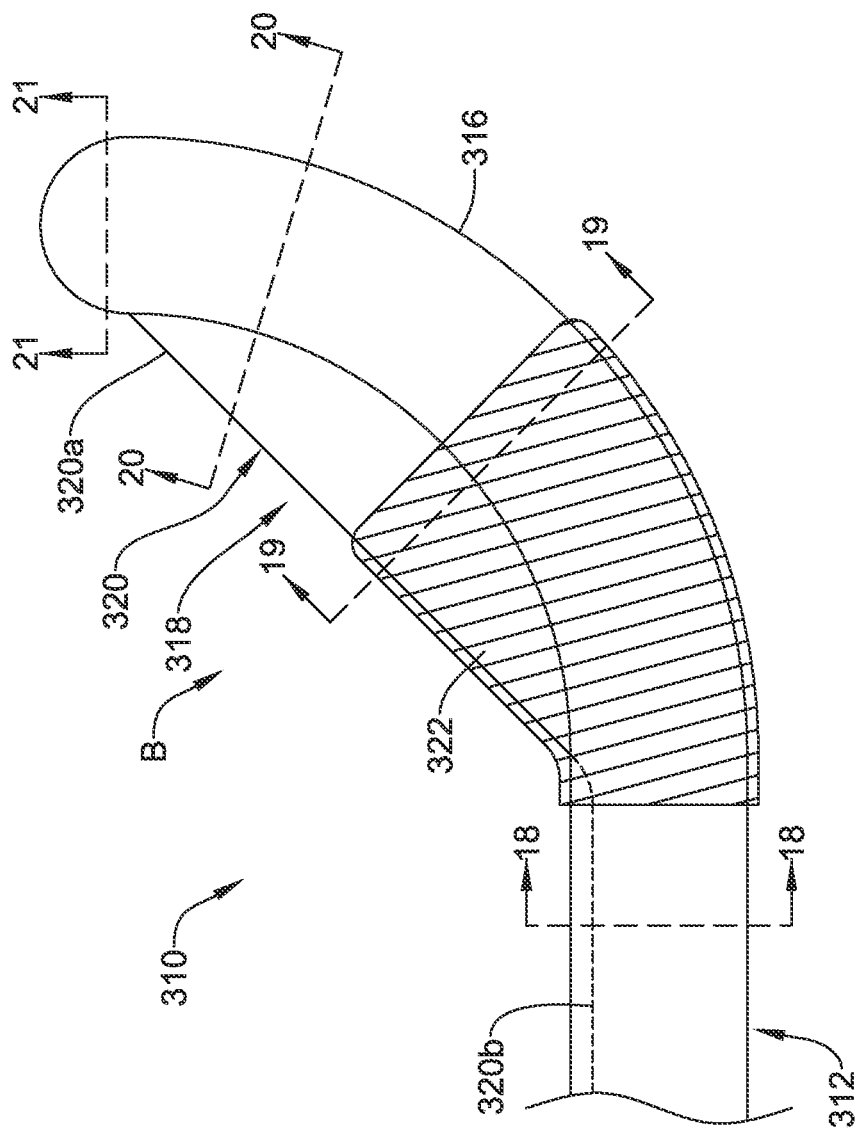
FIG. 17 is a side view of a portion of an example sphincterotome.
Figure 18:
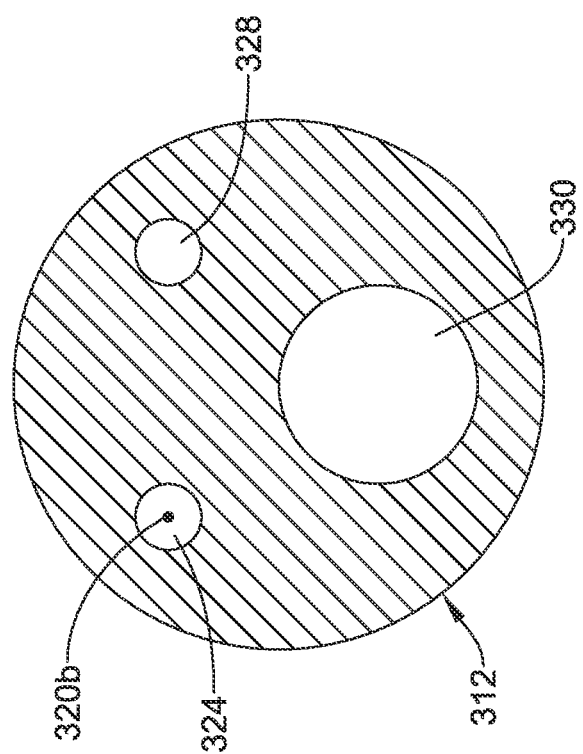
FIGS. 18-21 are cross-sectional views of the sphincterotome shown in FIG. 17.
Figure 19:
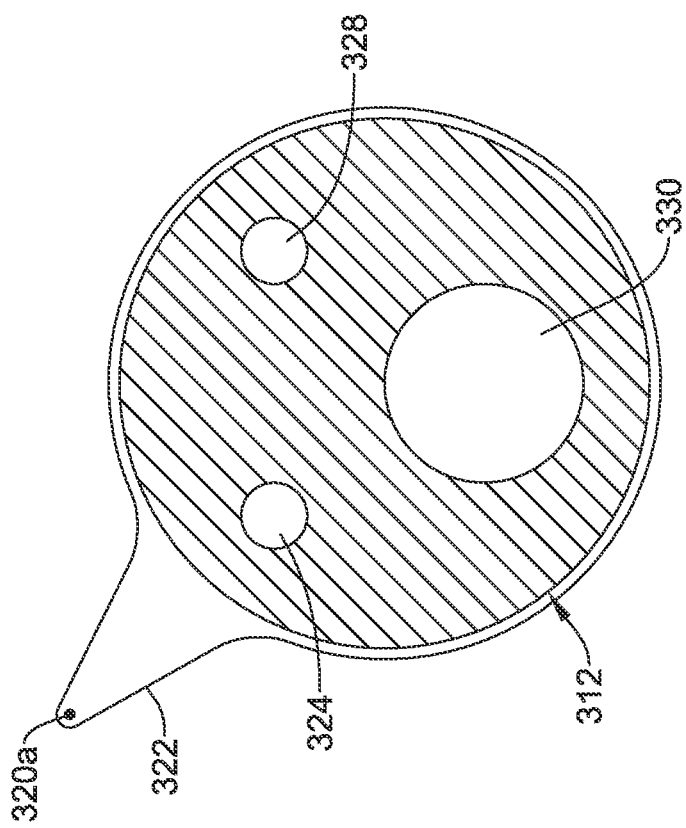
Figure 20:
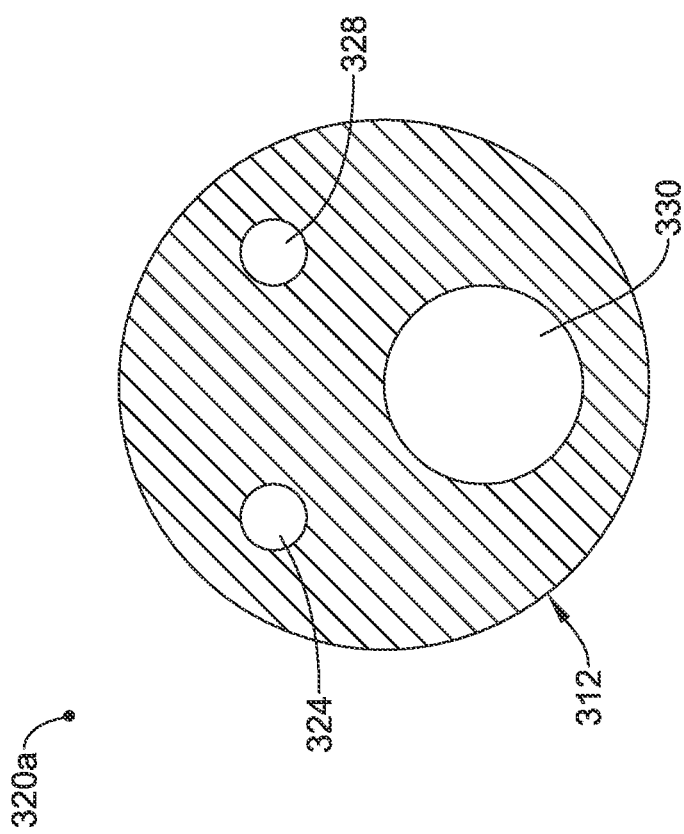
Figure 21:
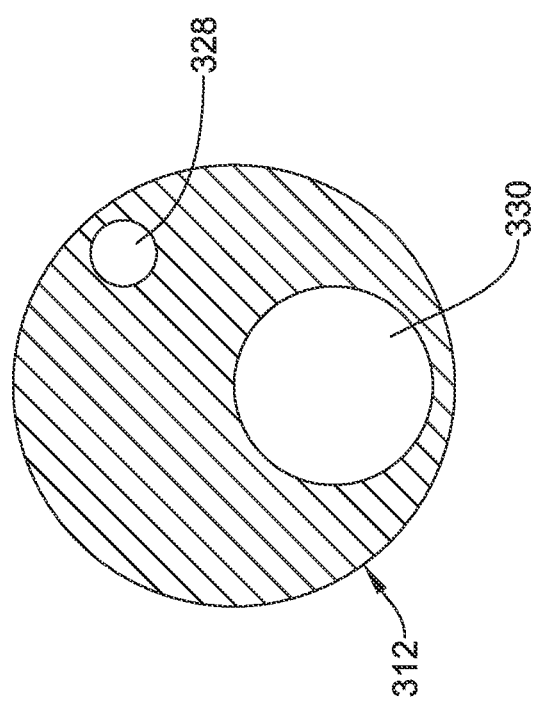

FIG. 17 illustrates another example sphincterotome 310 that may be similar in form and function to other sphincterotomes disclosed herein. The sphincterotome 310 includes a shaft 312 having a distal end region 316. The sphincterotome 310 may include a sphincterotome wire assembly 318. The sphincterotome wire assembly 318 may be designed to shift the distal end region 316 of the elongate shaft 312 between a first configuration and a curved or bowed configuration.

The sphincterotome wire assembly 318 may include a body portion B generally defined as the portion of the sphincterotome wire assembly 318 extending along the outer surface of the elongate shaft 312 and that may be described as extending diagonally akin to the string of a bow when the elongate shaft 312 is in the curved configuration. The sphincterotome wire assembly 318 may include a first member or portion 320 and a second member or portion 322. The first member 320 may take the form of a wire having a cutting region 320a and a proximally-extending region 320b. A distal end region of the first member 320 may be anchored to the distal end region 316 of the shaft 312. The second member 322 may take the form of a protective mesh or sheath designed to cover and/or insulate a portion of the first member 320.

The body portion B of the sphincterotome wire assembly 318 may include the cutting region 320a of the first member 320 and at least a portion of the second member 322. The cutting region 320a may be energized so as to facilitate cutting. The second member 322 may be non-conductive and insulate a portion of the first member 320 in a manner so as to not facilitate cutting.

FIGS. 18-21 are cross-sectional views taken at various locations along the shaft 312. Here it can be seen that the shaft 312 may include a number of different lumens. For example, the shaft 312 may include a first lumen 324, a second lumen 328, and a third lumen 330. In this example, the proximally-extending region 320b of the first member 320 may extend through the first lumen 324. The second lumen 328 may be used for infusing a fluid such as a contrast media. The third lumen 330 may be a guidewire lumen.

Figure 22:
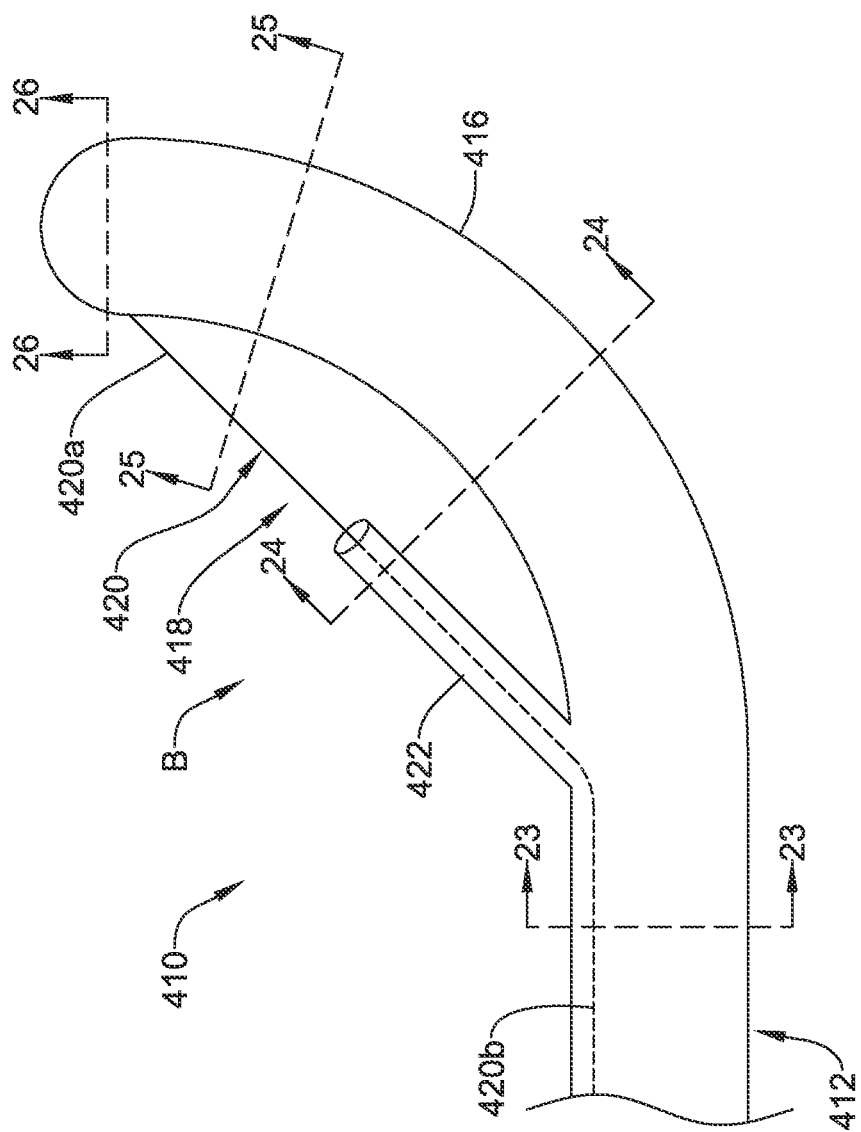
FIG. 22 is a side view of a portion of an example sphincterotome.
Figure 23:
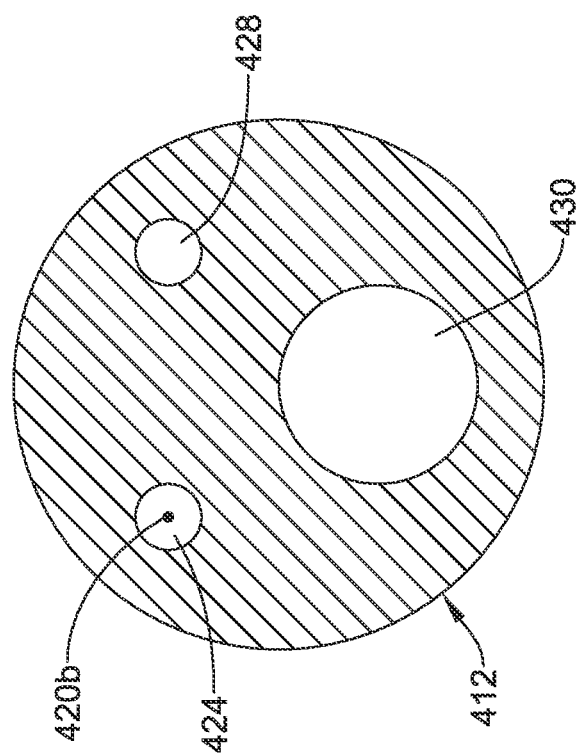
FIGS. 23-26 are cross-sectional views of the sphincterotome shown in FIG. 22.
Figure 24:
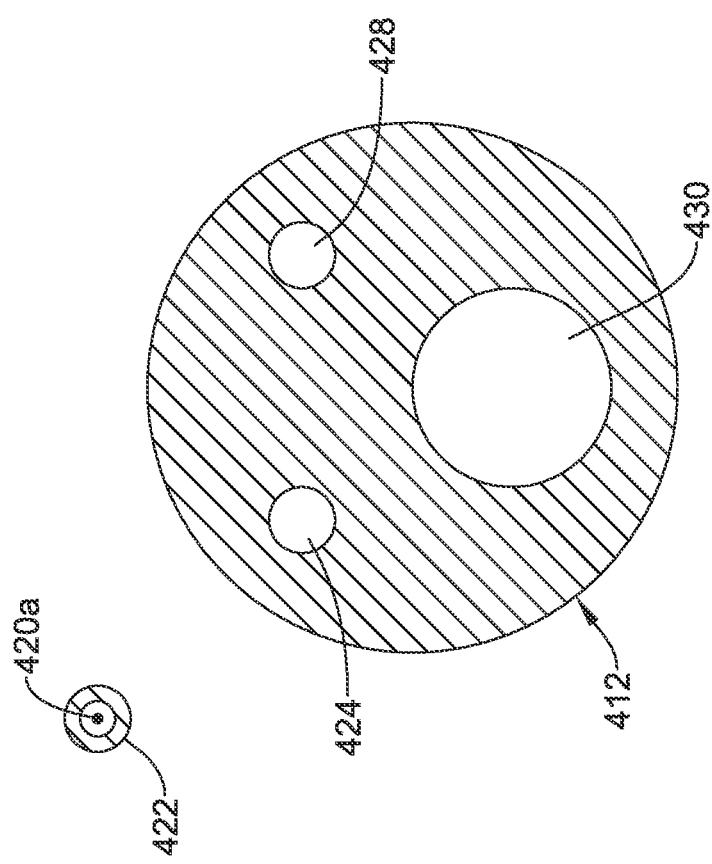
Figure 25:
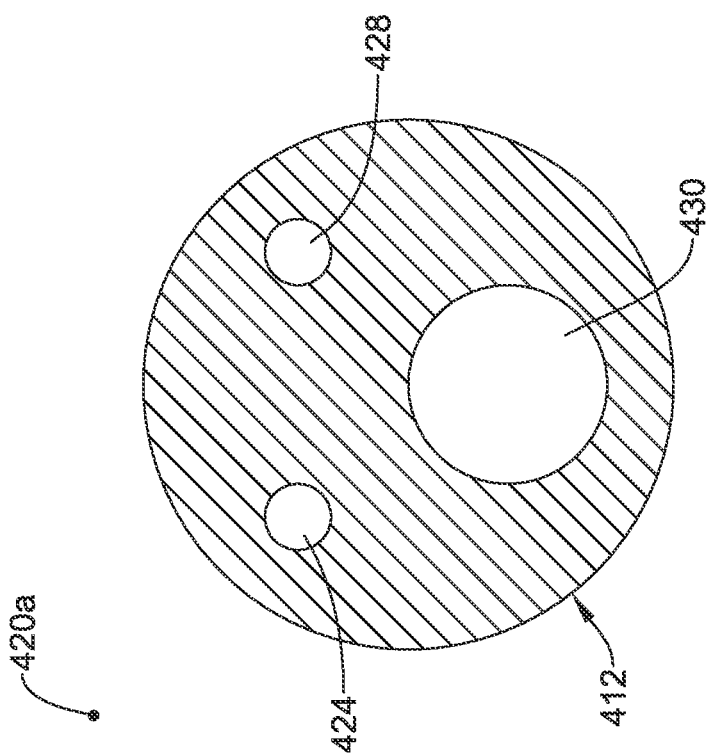
Figure 26:
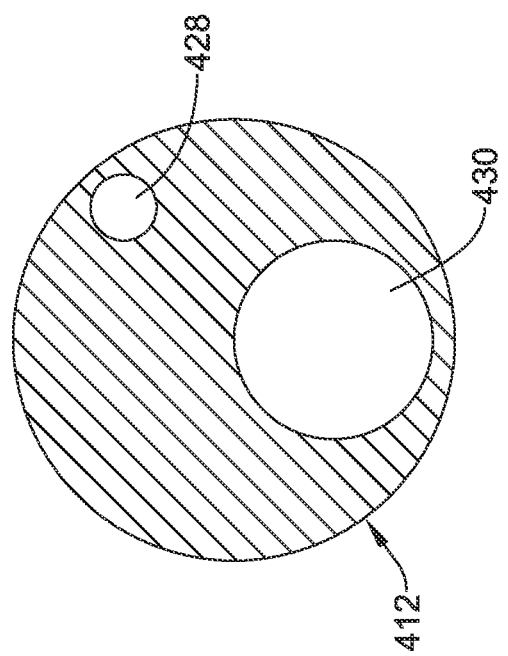

FIG. 22 illustrates another example sphincterotome 410 that may be similar in form and function to other sphincterotomes disclosed herein. The sphincterotome 410 includes a shaft 412 having a distal end region 416. The sphincterotome 410 may include a sphincterotome wire assembly 418. The sphincterotome wire assembly 418 may be designed to shift the distal end region 416 of the elongate shaft 412 between a first configuration and a curved or bowed configuration.

The sphincterotome wire assembly 418 may include a body portion B generally defined as the portion of the sphincterotome wire assembly 418 extending along the outer surface of the elongate shaft 412 and that may be described as extending diagonally akin to the string of a bow when the elongate shaft 412 is in the curved configuration. The sphincterotome wire assembly 418 may include a first member or portion 420 and a second member or portion 422. The first member 420 may take the form of a wire having a cutting region 420a and a proximally-extending region 420b. A distal end region of the first member 420 may be anchored to the distal end region 416 of the shaft 412. The second member 422 may take the form of a projection extending from the shaft 412. In general, the projection 422 is designed to cover and/or insulate a portion of the first member 420.

The body portion B of the sphincterotome wire assembly 418 may include the cutting region 420a of the first member 420 and at least a portion of the second member 422. The cutting region 420a may be energized so as to facilitate cutting. The second member 422 may be non-conductive and may cover and/or insulate a portion of the first member 420 in a manner so as to not facilitate cutting.

FIGS. 23-26 are cross-sectional views taken at various locations along the shaft 412. Here it can be seen that the shaft 412 may include a number of different lumens. For example, the shaft 412 may include a first lumen 424, a second lumen 428, and a third lumen 430. In this example, the proximally-extending region 420b of the first member 420 may extend through the first lumen 424. The second lumen 428 may be used for infusing a fluid such as a contrast media. The third lumen 430 may be a guidewire lumen.

Figure 27:
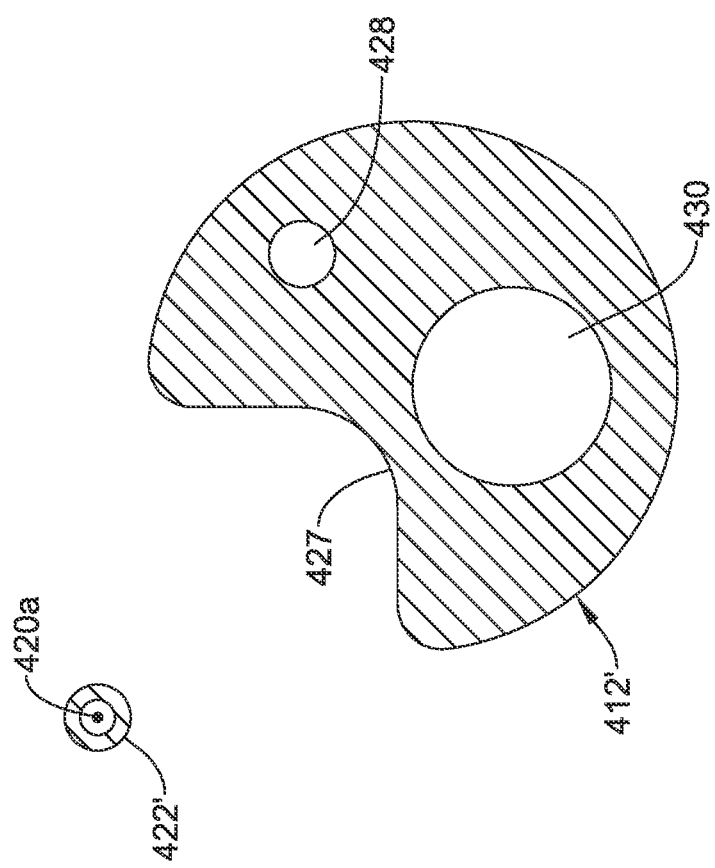
FIG. 27 is an alternative cross-section view of a portion of an example sphincterotome.

FIG. 27 is an alternative cross-sectional view of a portion of the shaft 412. In this example, the projection 422' is formed as a cutout from the shaft 412. Thus, the shaft 412 includes a cutout region 427. In some instances, the projection 422' may have a shape that mirrors or resembles the shape of the cutout region 427. In other instances, the projection 422' may be formed as a cutout and then processed to have a generally smaller shape and/or thickness.

Figure 28:
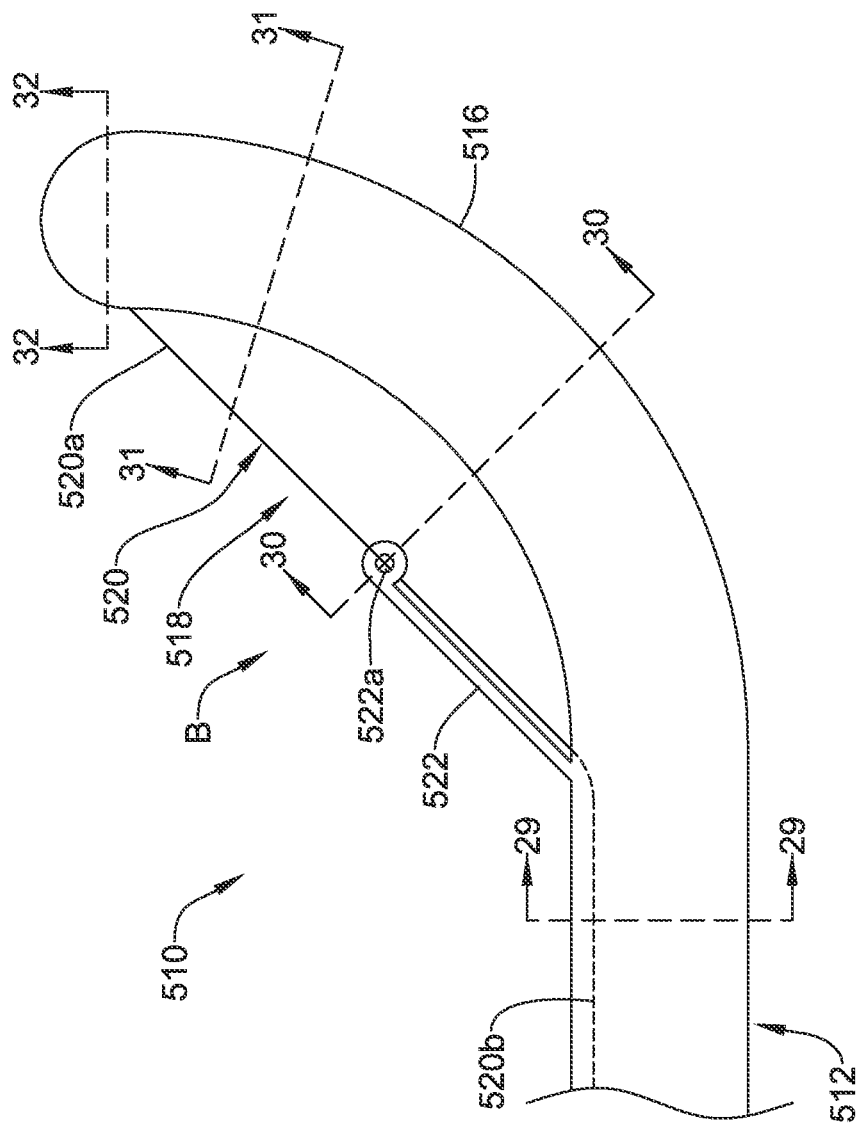
FIG. 28 is a side view of a portion of an example sphincterotome.
Figure 29:
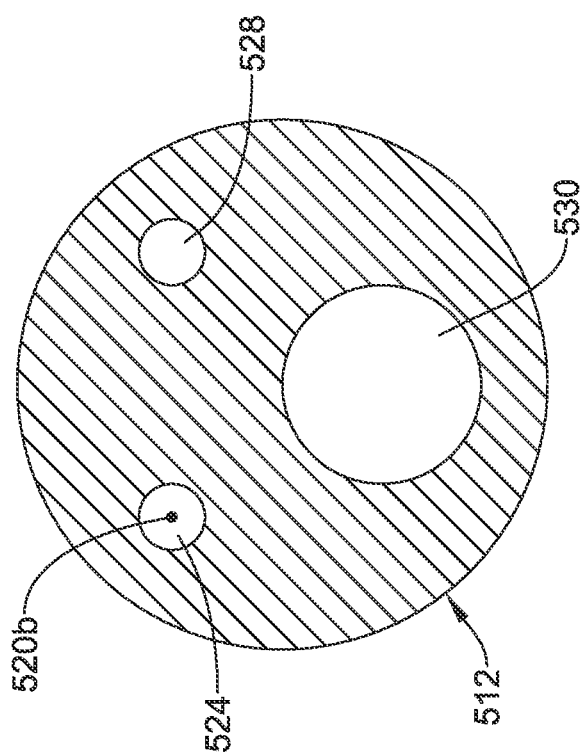
FIGS. 29-32 are cross-sectional views of the sphincterotome shown in FIG. 28.
Figure 30:
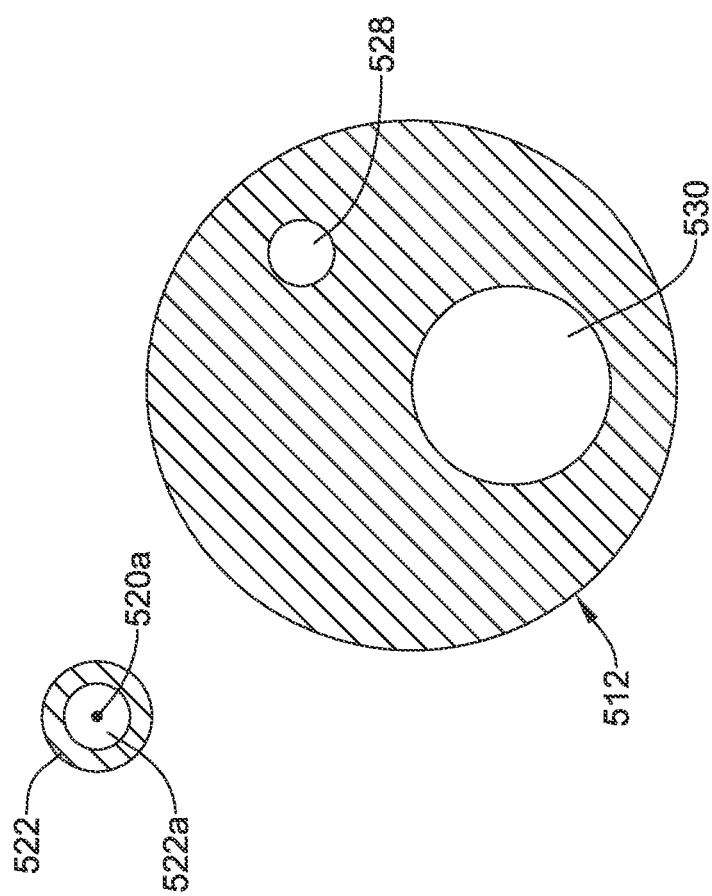
Figure 31:
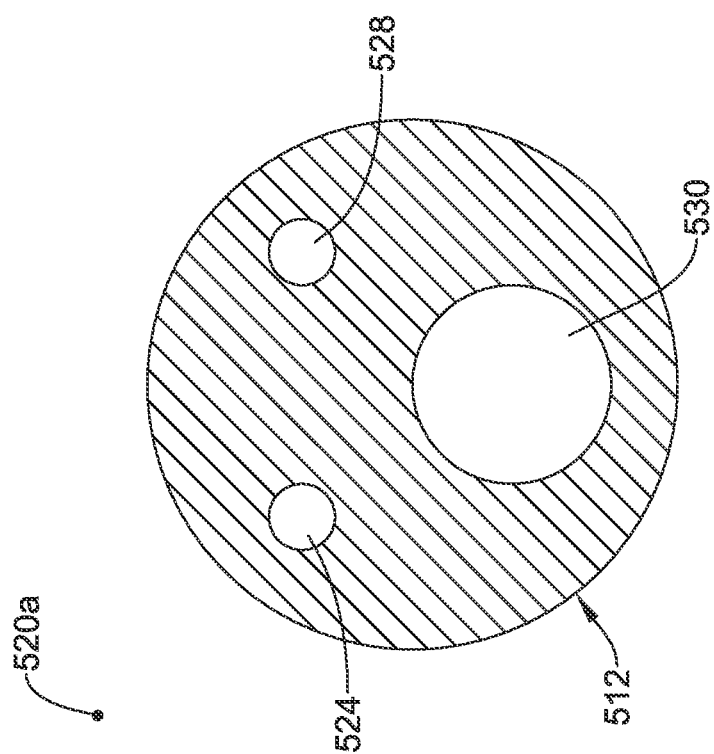
Figure 32:
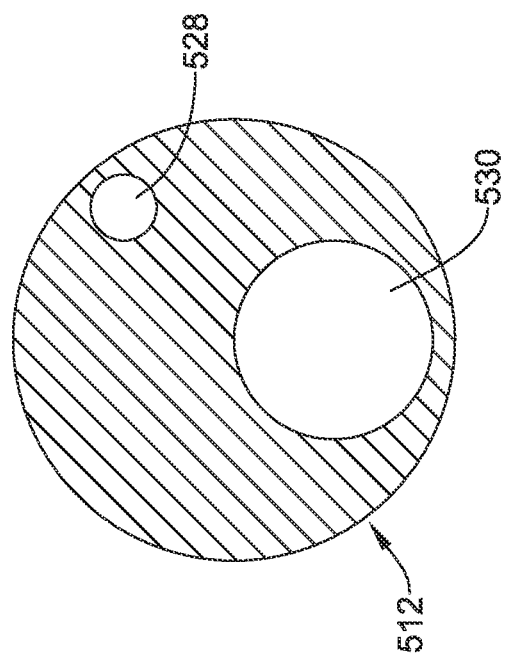

FIG. 28 illustrates another example sphincterotome 510 that may be similar in form and function to other sphincterotomes disclosed herein. The sphincterotome 510 includes a shaft 512 having a distal end region 516. The sphincterotome 510 may include a sphincterotome wire assembly 518. The sphincterotome wire assembly 518 may be designed to shift the distal end region 516 of the elongate shaft 512 between a first configuration and a curved or bowed configuration.

The sphincterotome wire assembly 518 may include a body portion B generally defined as the portion of the sphincterotome wire assembly 518 extending along the outer surface of the elongate shaft 512 and that may be described as extending diagonally akin to the string of a bow when the elongate shaft 512 is in the curved configuration. The sphincterotome wire assembly 518 may include a first member or portion 520 and a second member or portion 522. The first member 520 may take the form of a wire having a cutting region 520a and a proximally-extending region 520b. A distal end region of the first member 520 may be anchored to the distal end region 516 of the shaft 512. The second member 522 may take the form of a projection extending from the shaft 512. The projection 522 may include an opening 522a through which the first member 520 may extend. In general, the projection 522 is designed to cover and/or insulate a portion of the first member 520. In some instances, the projection 522 may include a slot or groove (not shown) through which the first member 520 may extend.

The body portion B of the sphincterotome wire assembly 518 may include the cutting region 520a of the first member 520 and at least a portion of the second member 522. The cutting region 520a may be energized so as to facilitate cutting. The second member 522 may be non-conductive and may cover and/or insulate a portion of the first member 520 in a manner so as to not facilitate cutting.

FIGS. 29-32 are cross-sectional views taken at various locations along the shaft 512. Here it can be seen that the shaft 512 may include a number of different lumens. For example, the shaft 512 may include a first lumen 524, a second lumen 528, and a third lumen 530. In this example, the proximally-extending region 520b of the first member 520 may extend through the first lumen 524. The second lumen 528 may be used for infusing a fluid such as a contrast media. The third lumen 530 may be a guidewire lumen.

Figure 33:
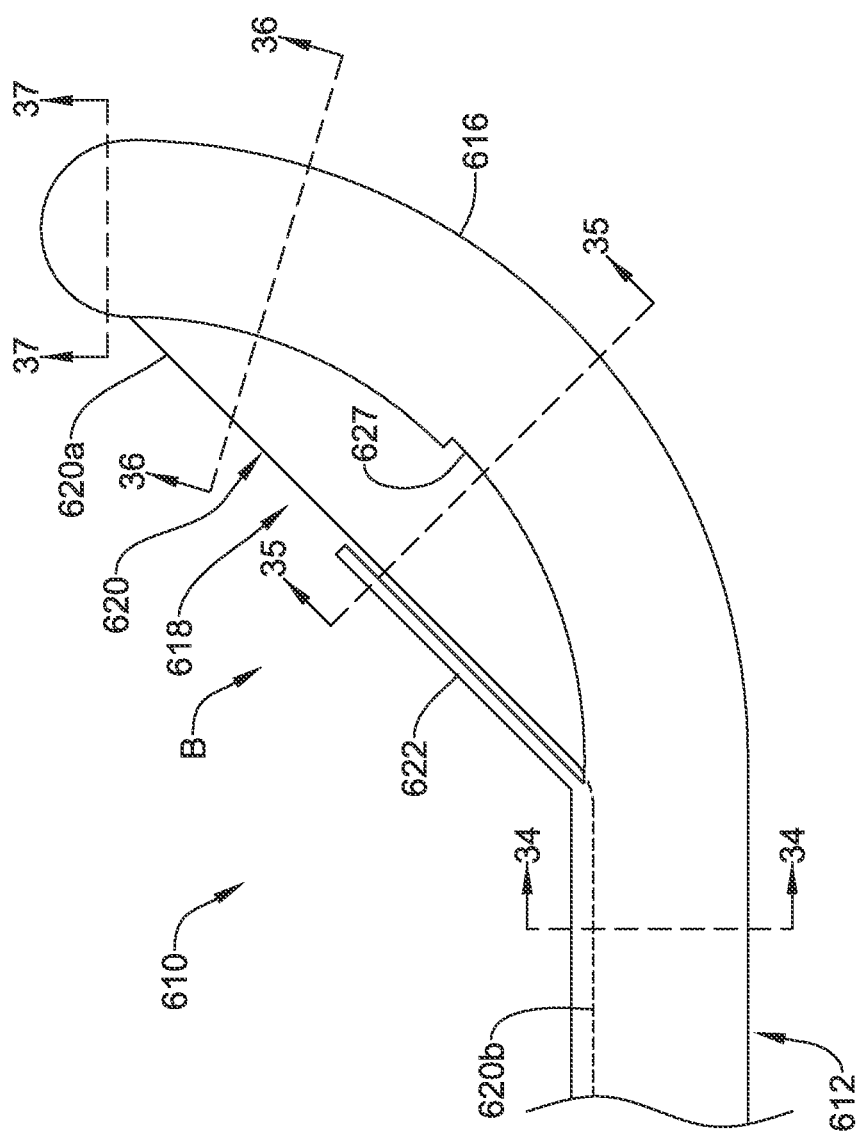
FIG. 33 is a side view of a portion of an example sphincterotome.
Figure 34:
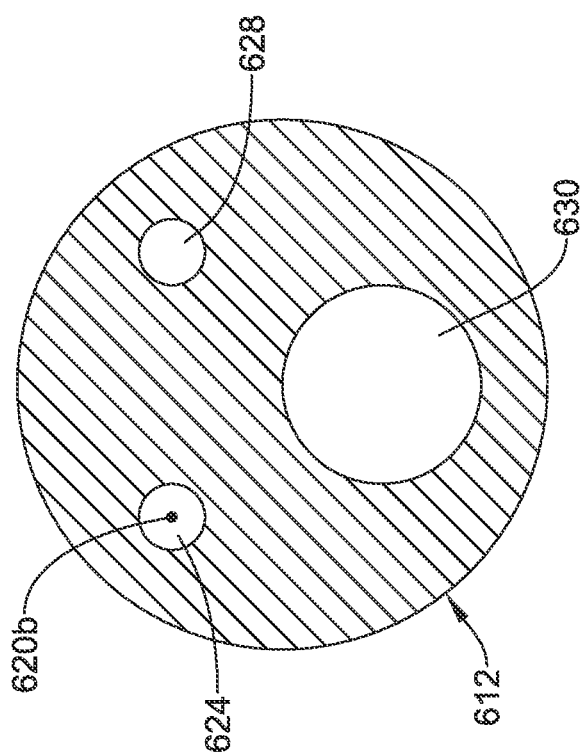
FIGS. 34-37 are cross-sectional views of the sphincterotome shown in FIG. 33.
Figure 35:
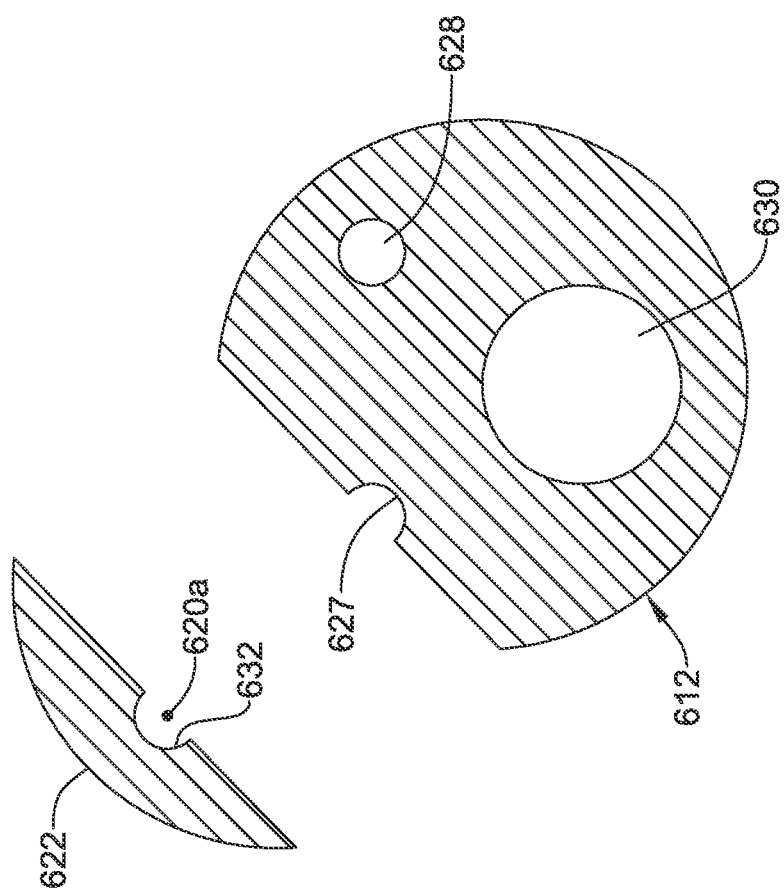
Figure 36:
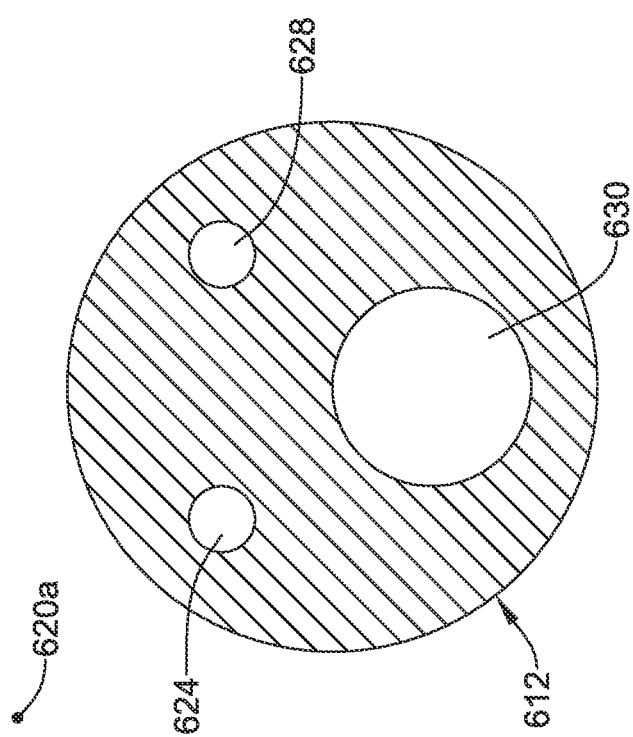
Figure 37:
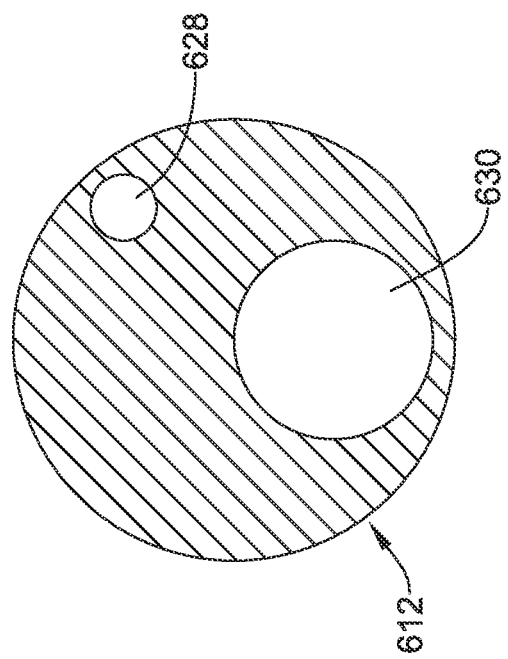

FIG. 33 illustrates another example sphincterotome 610 that may be similar in form and function to other sphincterotomes disclosed herein. The sphincterotome 610 includes a shaft 612 having a distal end region 616. The sphincterotome 610 may include a sphincterotome wire assembly 618. The sphincterotome wire assembly 618 may be designed to shift the distal end region 616 of the elongate shaft 612 between a first configuration and a curved or bowed configuration.

The sphincterotome wire assembly 618 may include a body portion B generally defined as the portion of the sphincterotome wire assembly 618 extending along the outer surface of the elongate shaft 612 and that may be described as extending diagonally akin to the string of a bow when the elongate shaft 612 is in the curved configuration. The sphincterotome wire assembly 618 may include a first member or portion 620 and a second member or portion 622. The first member 620 may take the form of a wire having a cutting region 620a and a proximally-extending region 620b. A distal end region of the first member 620 may be anchored to the distal end region 616 of the shaft 612. The second member 622 may take the form of a projection formed by a cutout in the shaft 612. The projection 622 may include a groove 632 through which the first member 620 may extend. The shaft 612 may include a notch 623 corresponding to where the projection 622 is cut out from the shaft 612. In general, the projection 622 is designed to insulate a portion of the first member 620.

The body portion B of the sphincterotome wire assembly 618 may include the cutting region 620a of the first member 620 and at least a portion of the second member 622. The cutting region 620a may be energized so as to facilitate cutting. The second member 622 may be non-conductive and may cover and/or insulate a portion of the first member 620 in a manner so as to not facilitate cutting.

FIGS. 34-37 are cross-sectional views taken at various locations along the shaft 612. Here it can be seen that the shaft 612 may include a number of different lumens. For example, the shaft 612 may include a first lumen 624, a second lumen 628, and a third lumen 630. In this example, the proximally-extending region 620b of the first member 620 may extend through the first lumen 624. The second lumen 628 may be used for infusing a fluid such as a contrast media. The third lumen 630 may be a guidewire lumen.

Figure 38:
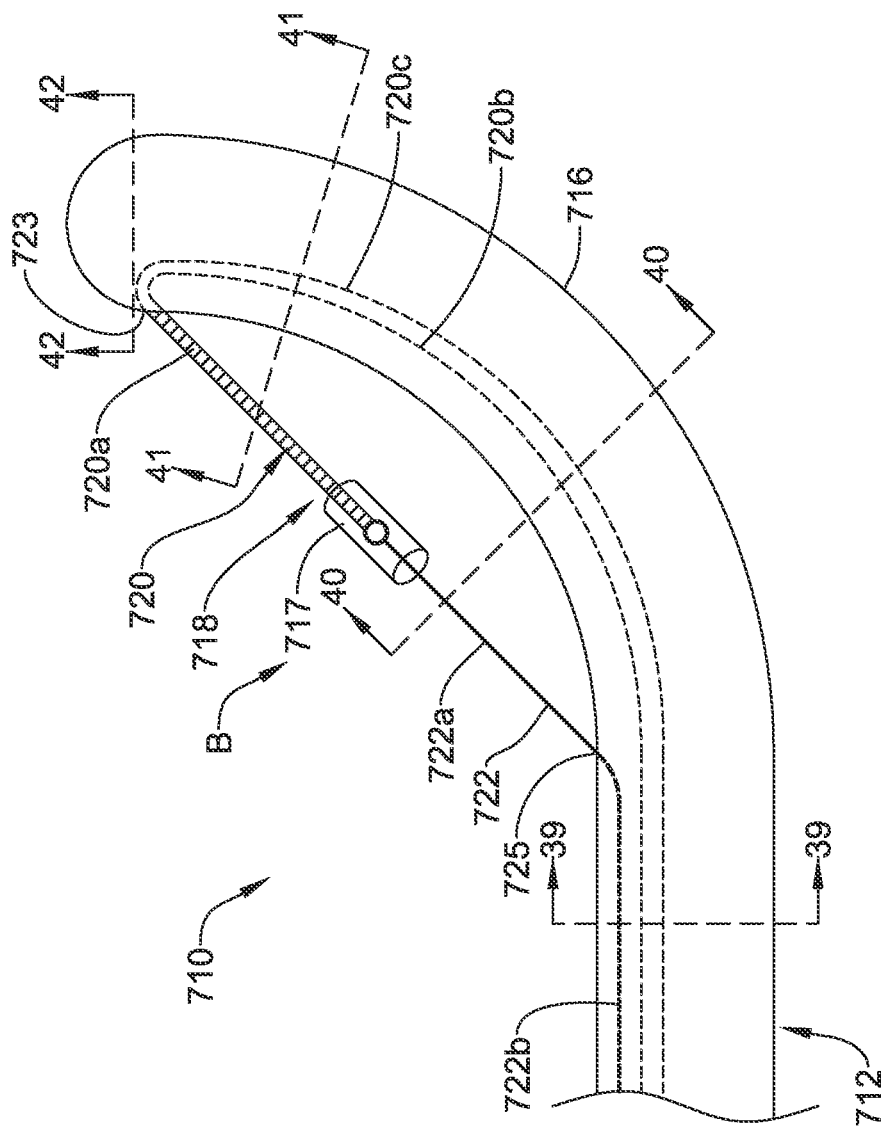
FIG. 38 is a side view of a portion of an example sphincterotome.

FIG. 38 illustrates another example sphincterotome 710 that may be similar in form and function to other sphincterotomes disclosed herein. The sphincterotome 710 includes a shaft 712 having a distal end region 716. The sphincterotome 710 may include a sphincterotome wire assembly 718. The sphincterotome wire assembly 718 may be designed to shift the distal end region 716 of the elongate shaft 712 between a first configuration and a curved or bowed configuration.

Figure 39:
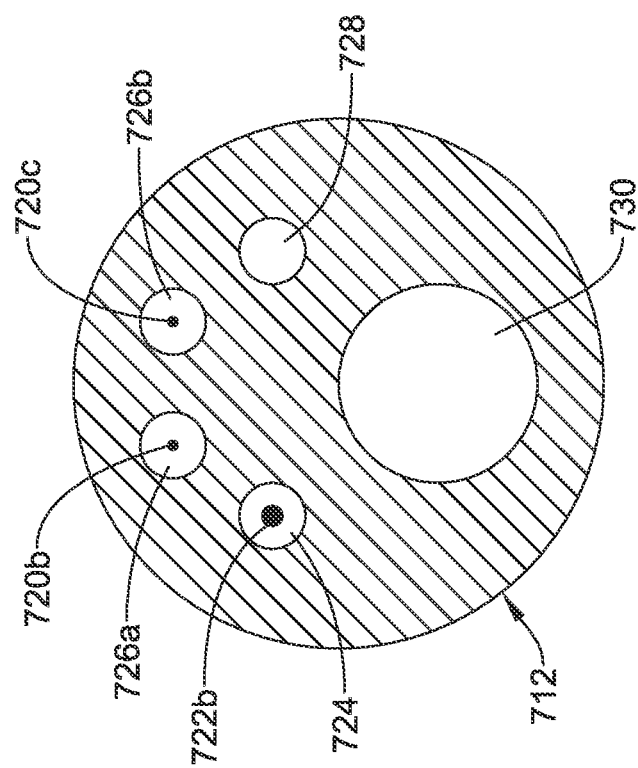
FIGS. 39-42 are cross-sectional views of the sphincterotome shown in FIG. 38.
Figure 40:
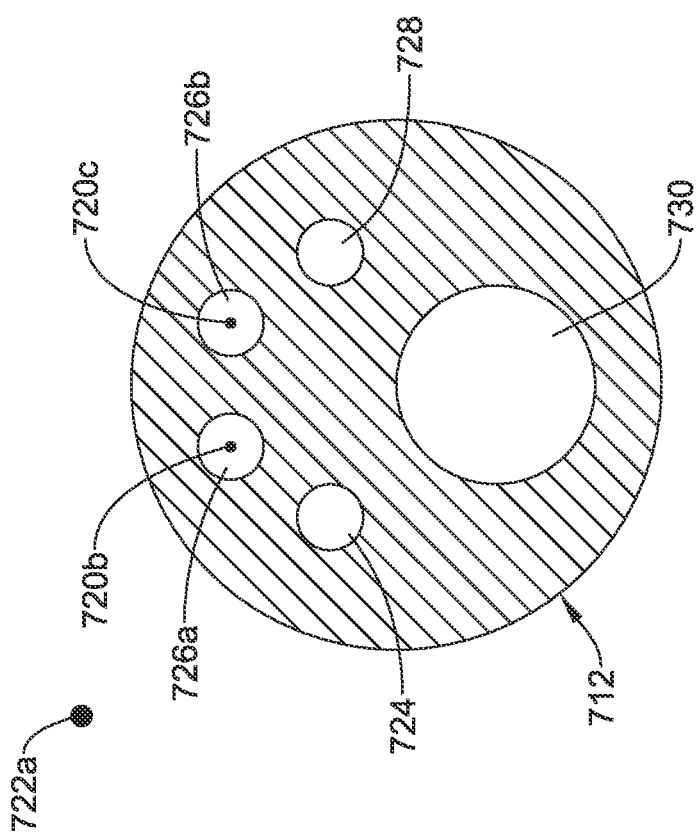
Figure 41:
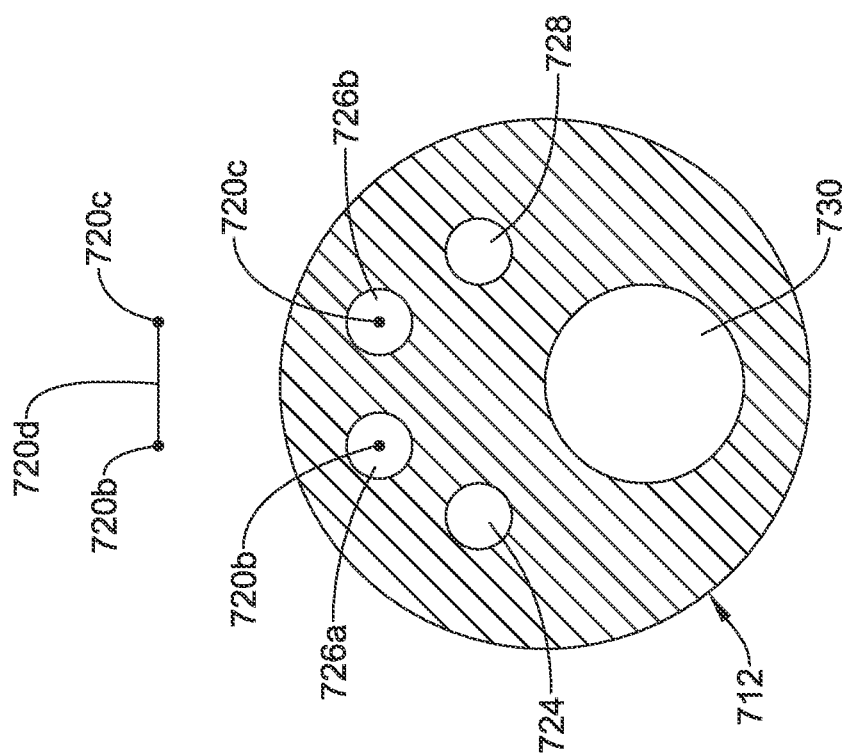
Figure 42:
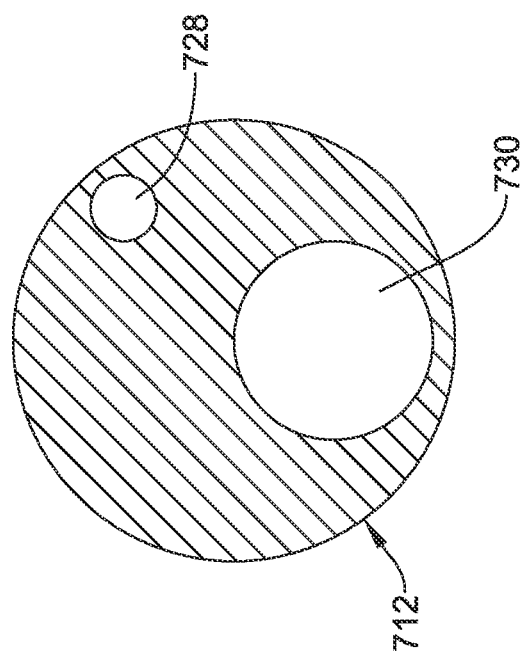

The sphincterotome wire assembly 718 may include a body portion B generally defined as the portion of the sphincterotome wire assembly 718 extending along the outer surface of the elongate shaft 712 and that may be described as extending diagonally akin to the string of a bow when the elongate shaft 712 is in the curved configuration. The sphincterotome wire assembly 718 may include a first member or portion 720 and a second member or portion 722. The first member 720 and the second member 722 may be coupled to one another at a joint 717. In this example, the joint 717 may take the form of an insulated housing or spacer. The first member 720 may take the form of a bipolar wire assembly having a cutting region 720a and a proximally-extending region that includes a first wire region 720b (e.g., a conductive wire) and a second wire region 720c (e.g., a ground wire). In insulating medium 720d may be disposed between the first wire region 720b and the second wire region 720c. The first wire region 720b and the second wire region 720c may extend through ports formed in the shaft 712 into lumens of the shaft 712 (e.g., a second lumen 726a and a third lumen 726b as shown in FIG. 39). The second member 722 may take the form of a wire or non-conductive cord having a non-conductive region 722a and a proximally-extending region 722b. The second member 722 may extend through a second port 725 formed in the shaft 712 and into a lumen of the shaft 712 (e.g., the first lumen 724 as shown, for example, in FIG. 39).

The body portion B of the sphincterotome wire assembly 718 may include the cutting region 720a of the first member 720 and at least a portion of the second member 722. The cutting region 720a may be energized so as to facilitate cutting. The second member 722 may be non-conductive and insulate a portion of the first member 720 in a manner so as to not facilitate cutting.

FIGS. 39-42 are cross-sectional views taken at various locations along the shaft 712. Here it can be seen that the shaft 712 may include a number of different lumens. For example, the shaft 712 may include a first lumen 724, a second lumen 726a, a third lumen 726b, a fourth lumen 728, and a fifth lumen 730. In this example, the proximally-extending region 722b of the second member 722 may extend through the first lumen 724. The first wire region 720b and the second wire region 720c of the first member 720 may extend through the second lumen 726a and the third lumen 726b, respectively. The fourth lumen 728 may be used for infusing a fluid such as a contrast media. The fifth lumen 730 may be a guidewire lumen.

Figure 43:
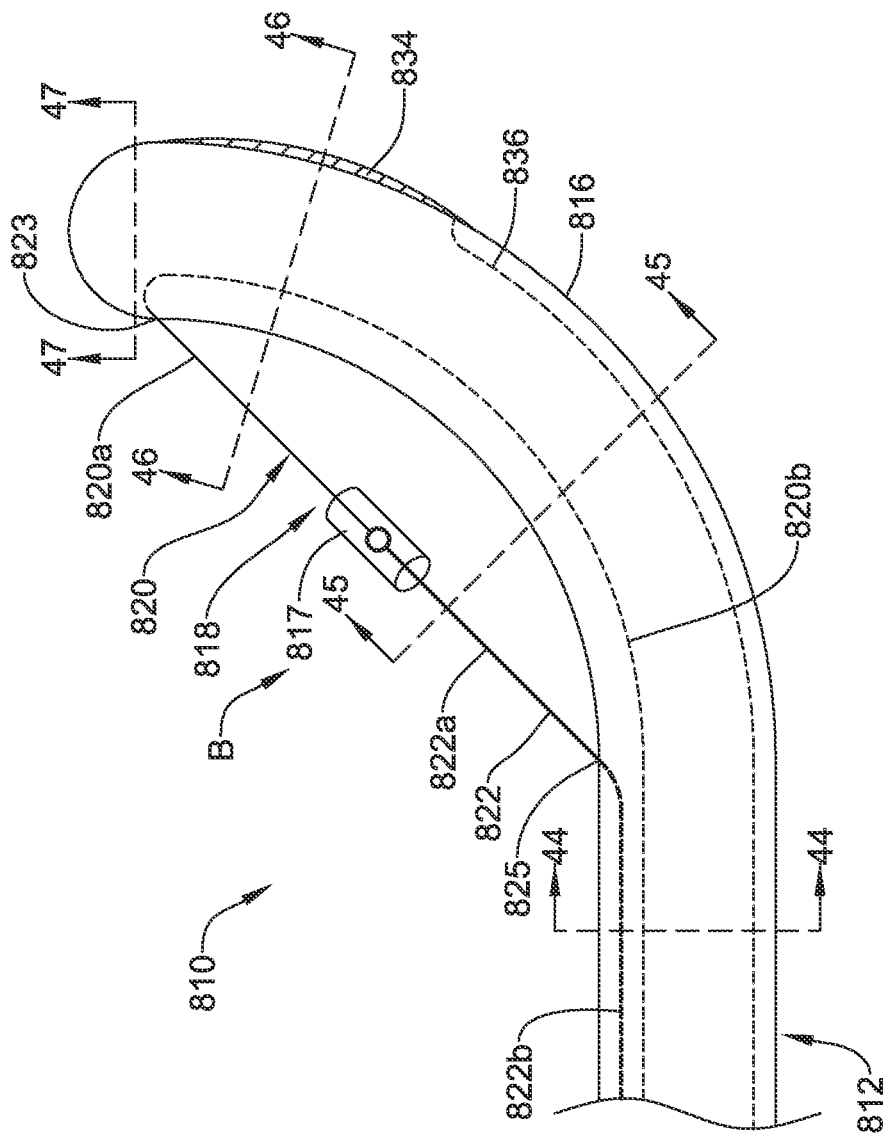
FIG. 43 is a side view of a portion of an example sphincterotome.
Figure 44:
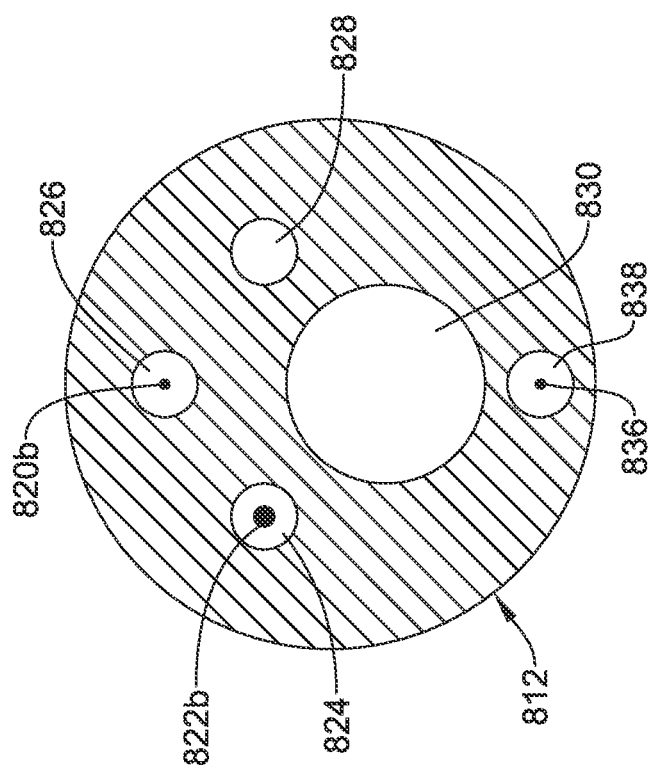
FIGS. 44-47 are cross-sectional views of the sphincterotome shown in FIG. 43.
Figure 45:
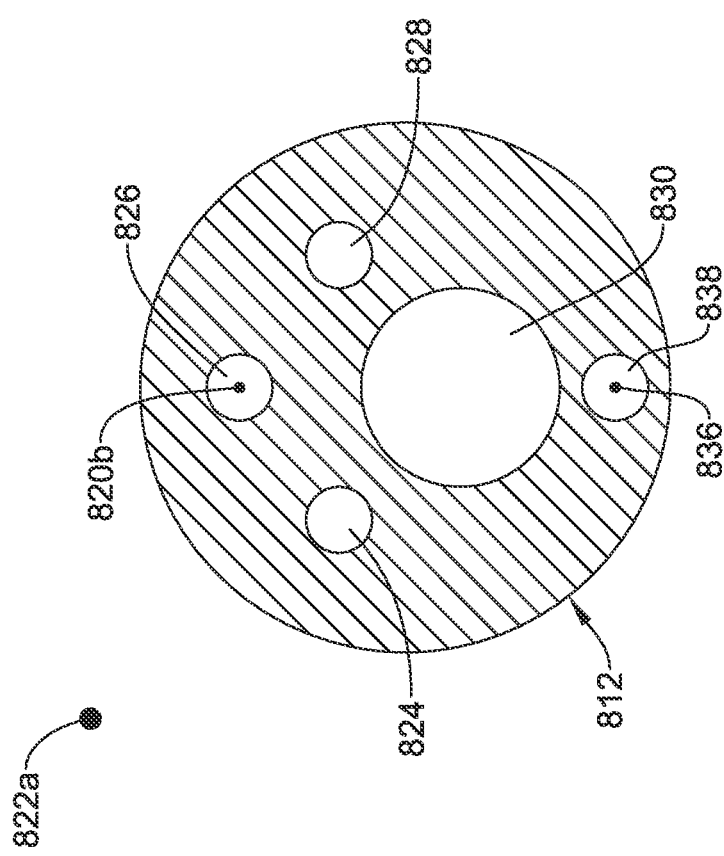
Figure 46:
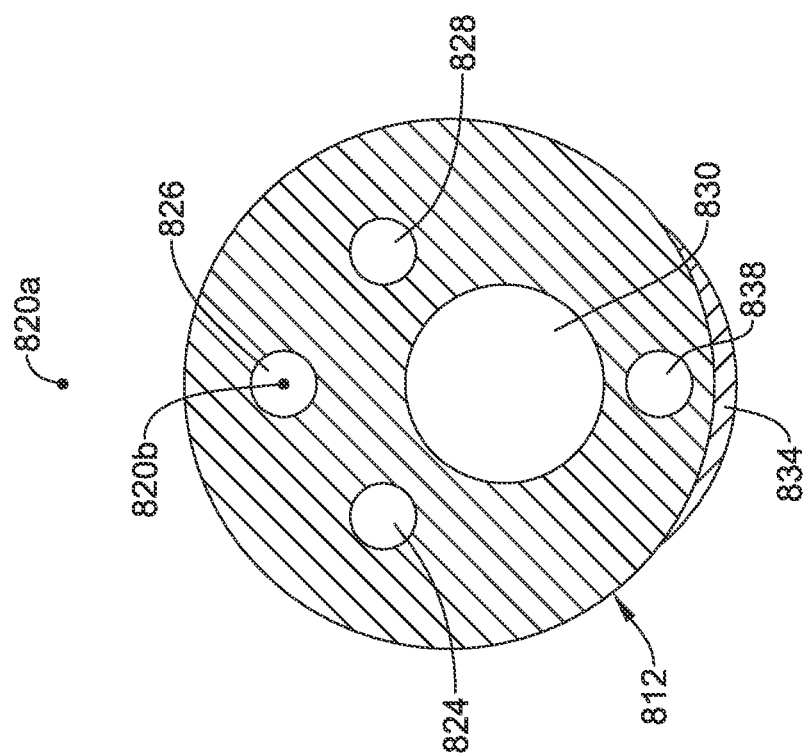
Figure 47:
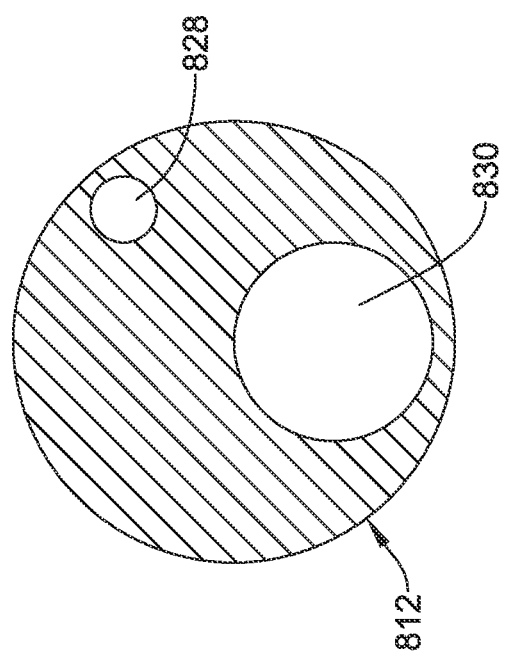

FIG. 43 illustrates another example sphincterotome 810 that may be similar in form and function to other sphincterotomes disclosed herein. The sphincterotome 810 includes a shaft 812 having a distal end region 816. The sphincterotome 810 may include a sphincterotome wire assembly 818. The sphincterotome wire assembly 818 may be designed to shift the distal end region 816 of the elongate shaft 812 between a first configuration and a curved or bowed configuration.

The sphincterotome wire assembly 818 may include a body portion B generally defined as the portion of the sphincterotome wire assembly 818 extending along the outer surface of the elongate shaft 812 and that may be described as extending diagonally akin to the string of a bow when the elongate shaft 812 is in the curved configuration. The sphincterotome wire assembly 818 may include a first member or portion 820 and a second member or portion 822. The first member 820 and the second member 822 may be coupled to one another at a joint 817. In this example, the joint 817 may take the form of an insulated housing. The first member 820 may take the form of a wire for delivering bipolar energy having a cutting region 820a and a proximally-extending region 820b. The first member 820 may extend through a first port 823 formed in the shaft 812 into a lumen of the shaft 812 (e.g., a second lumen 826 as shown in FIG. 43). The second member 822 may take the form of a wire or non-conductive cord having a non-conductive region 822a and a proximally-extending region 822b. The second member 822 may extend through a second port 825 formed in the shaft 812 and into a lumen of the shaft 812 (e.g., the first lumen 824 as shown, for example, in FIG. 43).

The body portion B of the sphincterotome wire assembly 818 may include the cutting region 820a of the first member 820 and at least a portion of the second member 8822. The cutting region 820a may be energized so as to facilitate cutting. In contrast, the second member 822 may be non-conductive. Accordingly, the non-conductive region 822a may generally be described as being non-energized, non-cutting, and/or otherwise designed so as to not facilitate cutting. A ground pad 834, which may serve as the return for the cutting wire portion 820a, may be disposed along the distal end region 816 of the shaft 812. A ground wire 836 may be coupled to the ground pad 834.

FIGS. 44-47 are cross-sectional views taken at various locations along the shaft 812. Here it can be seen that the shaft 812 may include a number of different lumens. For example, the shaft 812 may include a first lumen 824, a second lumen 826, a third lumen 828, a fourth lumen 830, and a fifth lumen 838. In this example, the proximally-extending region 820b of the first member 820 may extend through the second lumen 826. The proximally-extending region 822b of the second member may extend through the first lumen 824. The third lumen 828 may be used for infusing a fluid such as a contrast media. The fourth lumen 830 may be a guidewire lumen. The ground wire 836 may extend through the fifth lumen 838.

Figure 48:
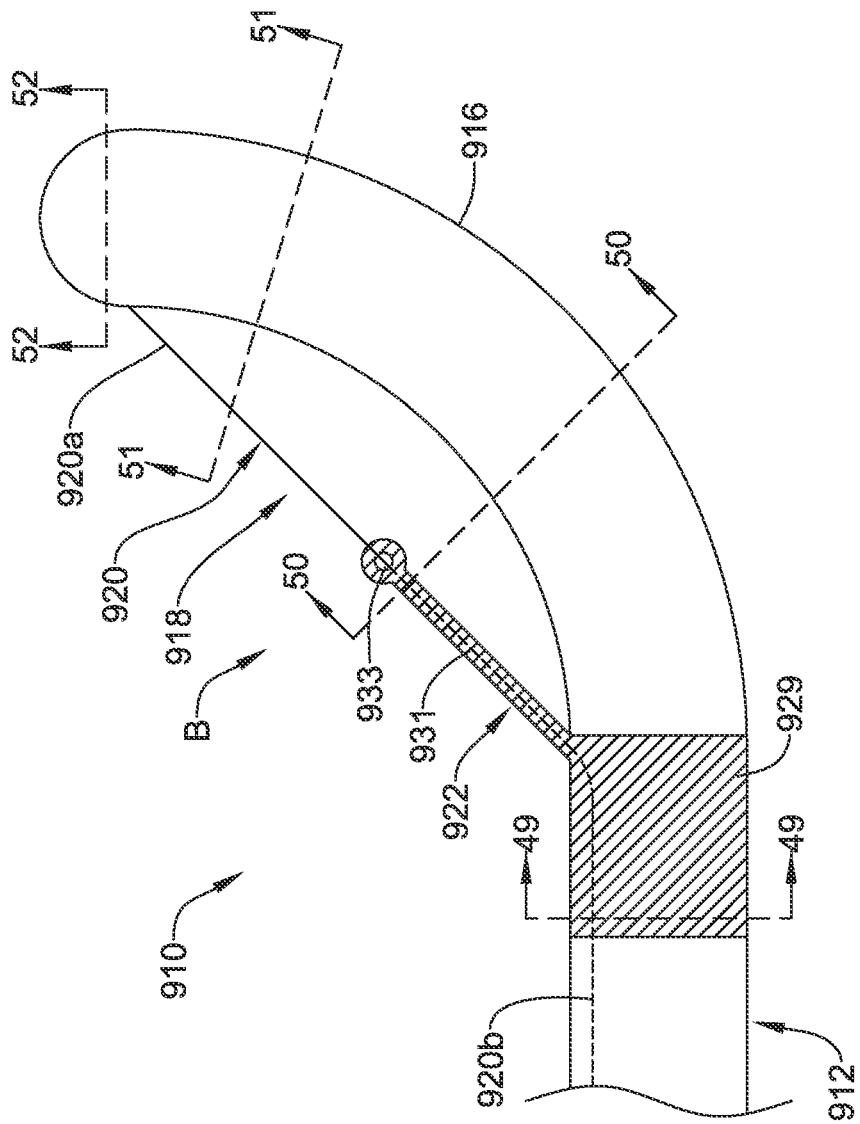
FIG. 48 is a side view of a portion of an example sphincterotome.
Figure 49:
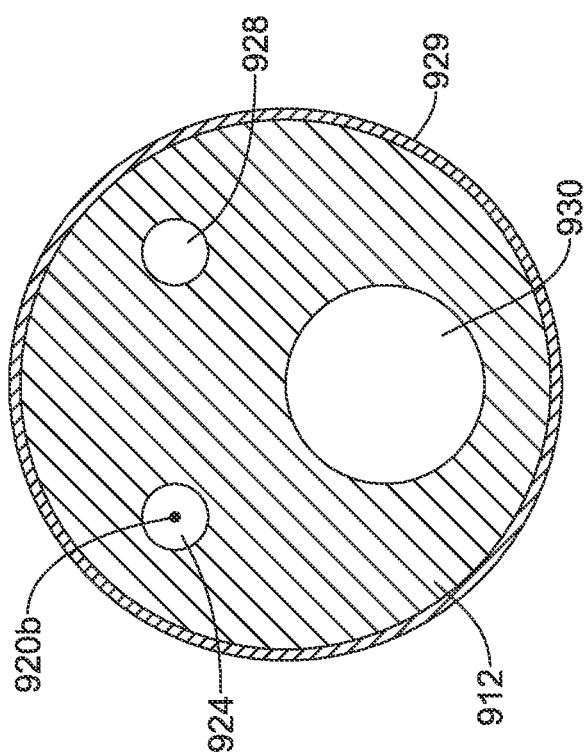
FIGS. 49-52 are cross-sectional views of the sphincterotome shown in FIG. 48.

FIG. 48 illustrates another example sphincterotome 910 that may be similar in form and function to other sphincterotomes disclosed herein. The sphincterotome 910 includes a shaft 912 having a distal end region 916. The sphincterotome 910 may include a sphincterotome wire assembly 918. The sphincterotome wire assembly 918 may be designed to shift the distal end region 916 of the elongate shaft 912 between a first configuration and a curved or bowed configuration.

The sphincterotome wire assembly 918 may include a body portion B generally defined as the portion of the sphincterotome wire assembly 918 extending along the outer surface of the elongate shaft 912 and that may be described as extending diagonally akin to the string of a bow when the elongate shaft 912 is in the curved configuration. The sphincterotome wire assembly 918 may include a first member or portion 920 and a second member or portion 922. The first member 920 may take the form of a wire having a cutting region 920a and a proximally-extending region 920b. A distal end region of the first member 920 may be anchored to the distal end region 916 of the shaft 912.

Figure 50:
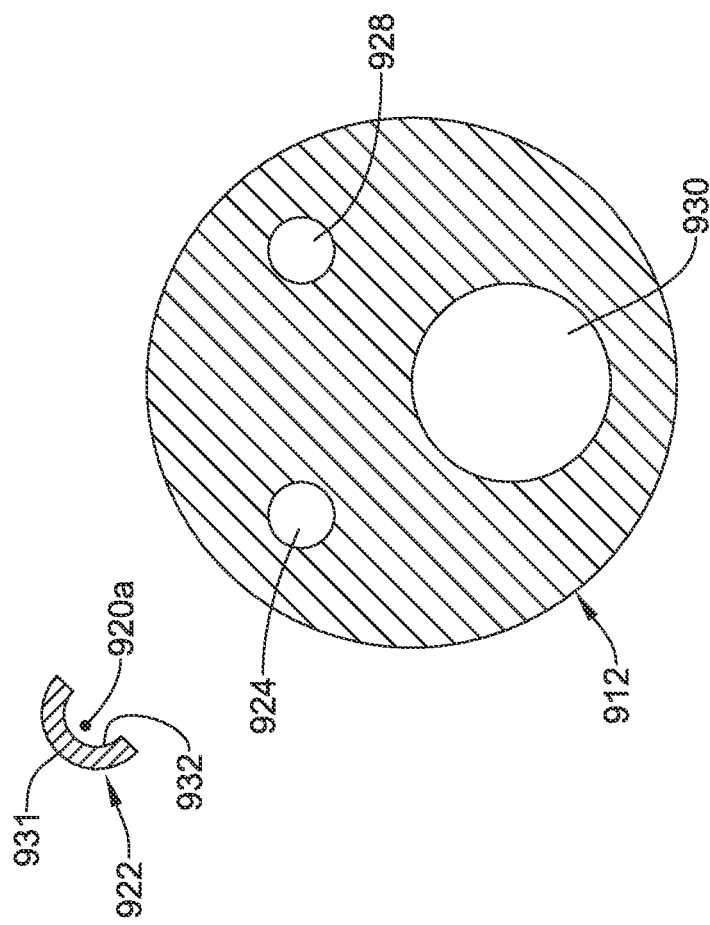
Figure 51:
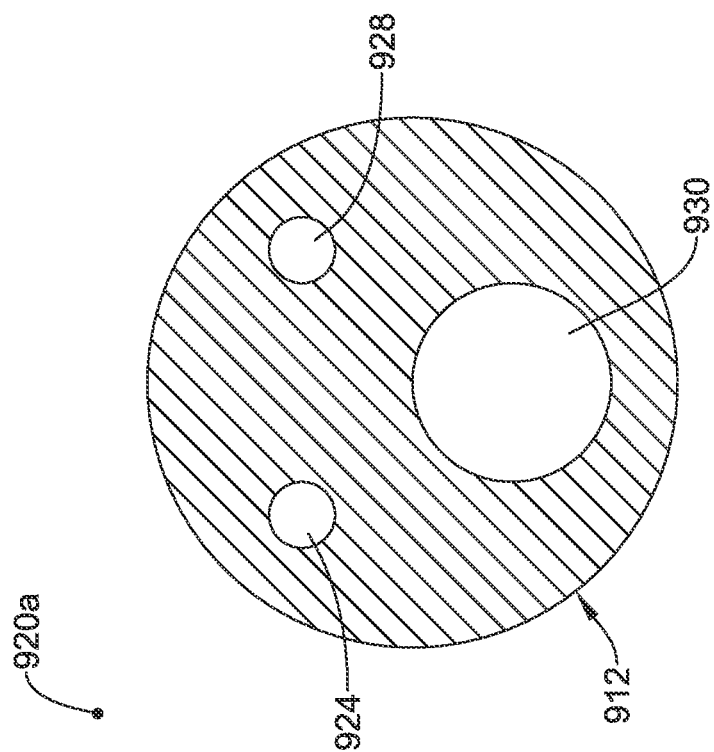
Figure 52:
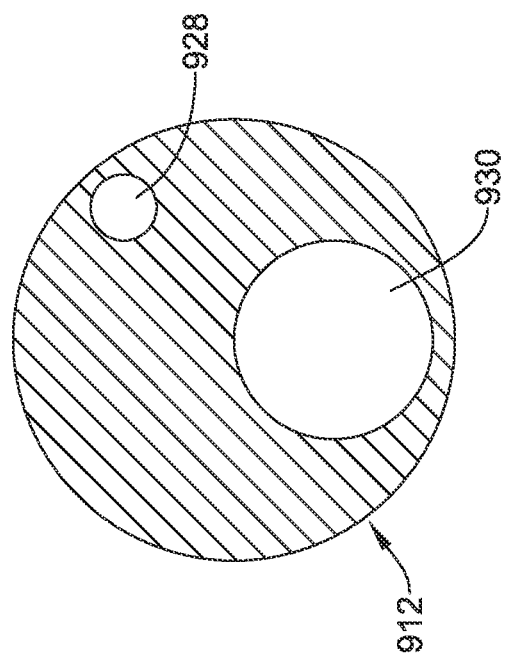

The second member 922 may take the form of an external flap coupled to the shaft 912 (e.g., coupled via an adhesive bond, thermal bond, and/or the like). The second member 922 may be formed of a suitable material such as a polymer (e.g., polyetheretherketone and/or any suitable disclosed herein). The flap 622 may include a body region 929 disposed along the outer surface of the shaft 912, a projection region 931 extending from the body region 929, and an end region 933. The projection region 931 may have a suitable length such as about 1-20 mm, or about 2-18 mm, or about 5-15 mm. In some instances, the projection region 931 may include a groove 932 (not shown in FIG. 48, can be seen in FIG. 50) through which the first member 920 may extend. In some of these and in other instances, the end region 933 may include or otherwise take the form of a loop or opening through which the first member 920 may extend.

The body portion B of the sphincterotome wire assembly 918 may include the cutting region 920a of the first member 920 and at least a portion of the second member 922 (e.g., the projection region 931). The cutting region 920a may be energized so as to facilitate cutting. The second member 922 may be non-conductive and may cover and/or insulate a portion of the first member 920 in a manner so as to not facilitate cutting. More particularly, the projection region 931 (and/or the second member 922) may be designed to insulate a portion of the first member 920.

It can be appreciated that the length of the first member 920 that is exposed or otherwise not covered/insulated by the projection region 931 can vary depending on the extent to which the shaft 912 is curved. For example, a clinician may be able to curve the shaft 912 to a relative small extent. When doing so, only a relatively small proportion of the length of the first member 920 may be covered/insulated by the projection region 931. Further curving the shaft 912 may shorten the overall length of the first member 920 along the body region B and increase the proportion of the length of the first member 920 that is covered/insulated by the projection region 931. This allows a clinician to vary the length of the first member 920 available for cutting, which may be desirable in order to tailor the sphincterotome 910 for a number of different interventions.

FIGS. 49-52 are cross-sectional views taken at various locations along the shaft 912. Here it can be seen that the shaft 912 may include a number of different lumens. For example, the shaft 912 may include a first lumen 924, a second lumen 928, and a third lumen 930. In this example, the proximally-extending region 920b of the first member 920 may extend through the first lumen 924. The second lumen 928 may be used for infusing a fluid such as a contrast media. The third lumen 930 may be a guidewire lumen.

Figure 53:
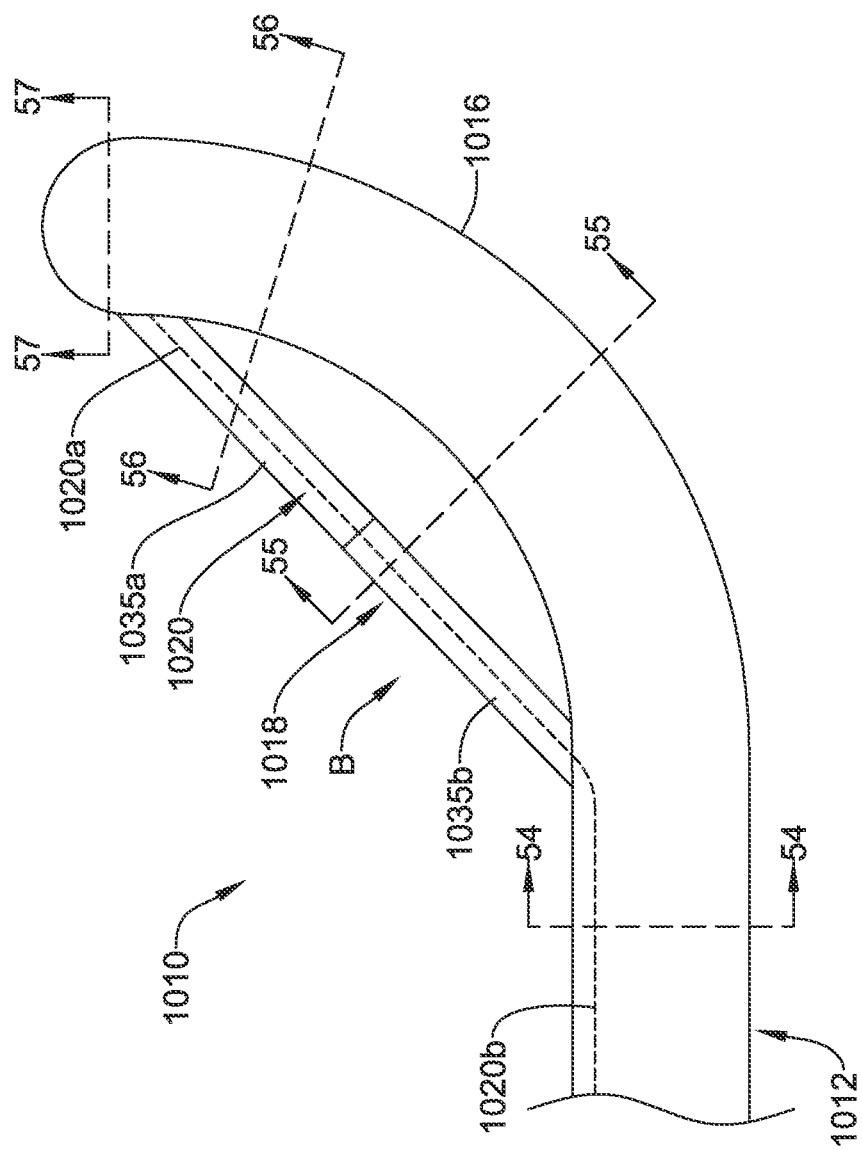
FIG. 53 is a side view of a portion of an example sphincterotome.
Figure 54:
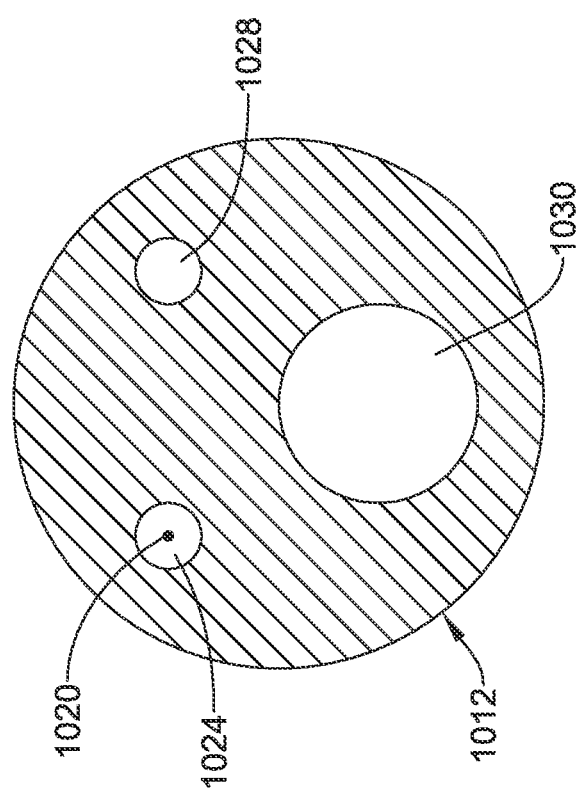
FIGS. 54-57 are cross-sectional views of the sphincterotome shown in FIG. 53.
Figure 55:
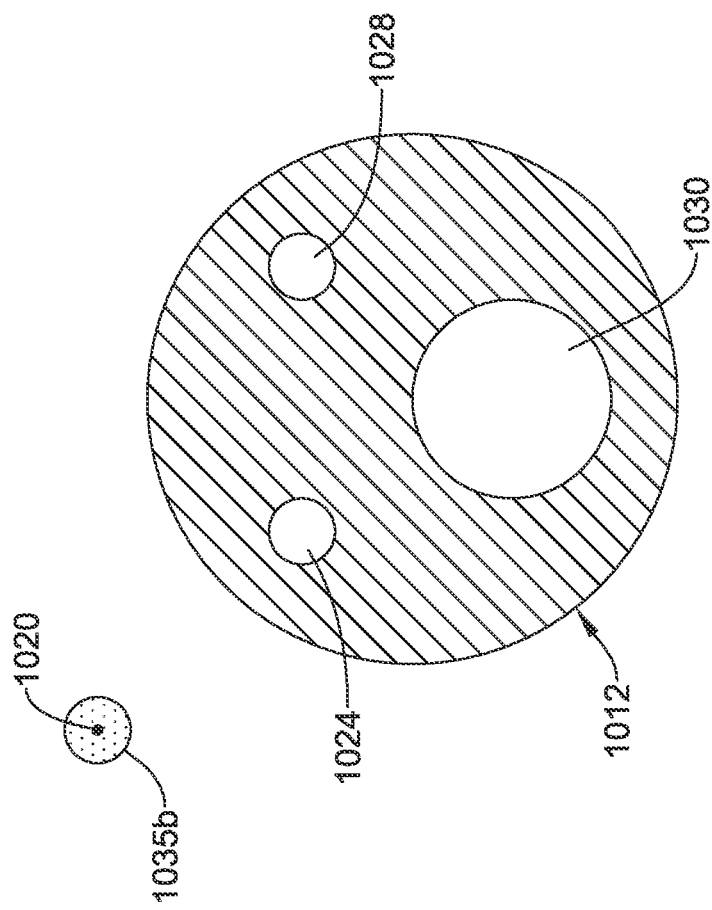
Figure 56:
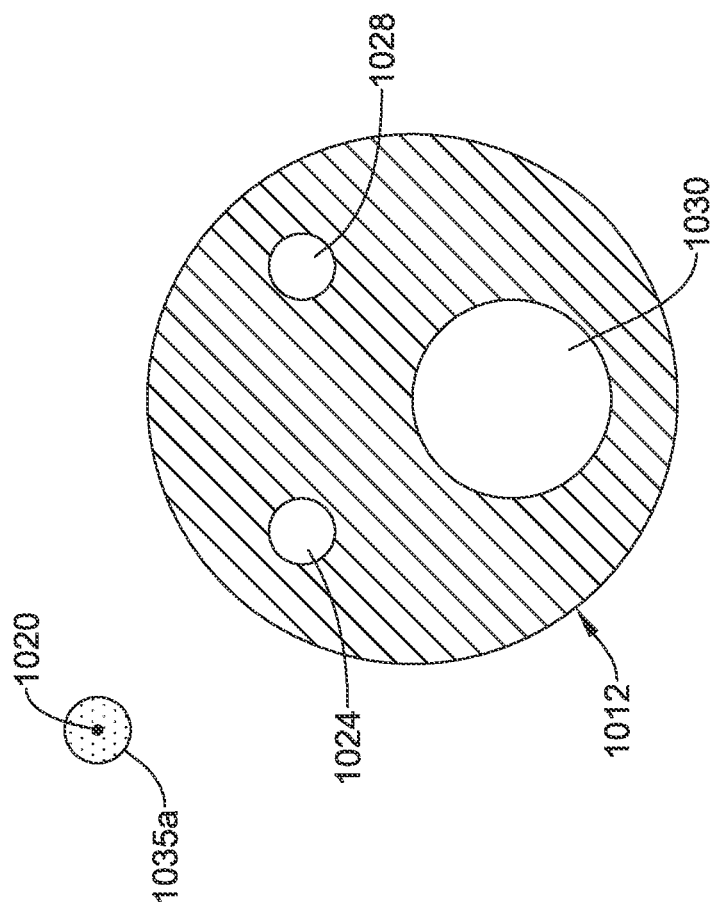
Figure 57:
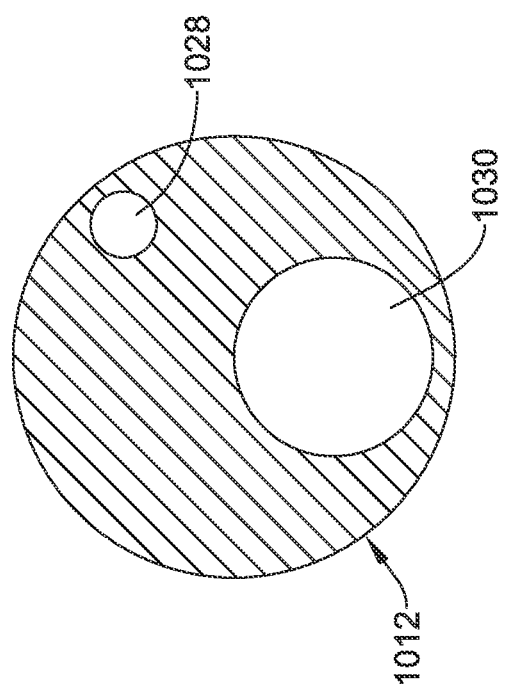

FIG. 53 illustrates another example sphincterotome 1010 that may be similar in form and function to other sphincterotomes disclosed herein. The sphincterotome 1010 includes a shaft 1012 having a distal end region 1016. The sphincterotome 1010 may include a sphincterotome wire assembly 1018. The sphincterotome wire assembly 918 may be designed to shift the distal end region 1016 of the elongate shaft 1012 between a first configuration and a curved or bowed configuration.

The sphincterotome wire assembly 1018 may include a body portion B generally defined as the portion of the sphincterotome wire assembly 1018 extending along the outer surface of the elongate shaft 1012 and that may be described as extending diagonally akin to the string of a bow when the elongate shaft 1012 is in the curved configuration. The sphincterotome wire assembly 1018 may include a first member or wire 1020 having a cutting region 1020a and a proximally-extending region 1020b. A distal end region of the wire 1020 may be anchored to the distal end region 1016 of the shaft 1012. A plurality of different coatings may be disposed along the wire 1020. For example, a first coating 1035a may be disposed along a first portion (e.g., a more distal portion) of the wire 1020 and a second or coating 1035b may be disposed along a second portion (e.g., a more proximal portion) of the wire 1020. The first coating 1035a, the second coating 1035b, or both may be disposed along the wire 1020 using a suitable process. Some example processes that may be suitable include electroplating, sputter coating, dip coating, spray coating, other coating processes, and/or the like.

In some instances, the first coating 1035a may be a conductive coating. For example, the first coating 1035a may have a relatively high conductivity (e.g., on the order of about $1\times10^6$ Siemens/m or greater) and a relatively low resistivity (e.g., on the order of about $7\times10^{-7}$ Ohms/m or less). In some instances, the first coating 1035a may include a metallic coating such as a gold coating. Other coatings are contemplated.

In some instances, the second coating 1035b may be a non-conductive or insulating coating that, in general, is designed to insulate a second portion of the wire 1020. For example, the second coating 1035b may have a relatively low conductivity (e.g., on the order of about $1\times10^6$ Siemens/m or less) and a relatively high resistivity (e.g., on the order of about $7\times10^{-7}$ Ohms/m or greater). For example, the second coating 1035b may include a ceramic coating, a polymeric coating, metal oxide (e.g., such as aluminum oxide), a metal nitride, and/or the like.

The body portion B of the sphincterotome wire assembly 1018 may include the cutting region 1020a of the wire 1020. The cutting region 1020a may be energized so as to facilitate cutting. When doing so, the first coating 1035a can conduct energy to facilitate cutting. The second coating 1035b may be non-conductive and may cover and/or insulate the wire 1020 in a manner so as to not facilitate cutting. It can be appreciated that variations in the difference in conductivity between the first coating 1035a and the second coating 1035b may alter the cutting characteristics of the sphincterotome wire assembly 1018. For example, relatively large differences in conductivity between the first coating 1035a and the second coating 1035b may generate more aggressive tissue burns at positions more adjacent to the first coating 1035a and less aggressive tissue burns (e.g., or no tissue burns) at positions more adjacent to the second coating 1035b. Relatively small differences in conductivity between the first coating 1035a and the second coating 1035b may result in more evenly distributed burns along the sphincterotome wire assembly 1018. In some instances, the first coating 1035a, the second coating 1035b, or both may terminate adjacent to the outer surface of the shaft 1012.

FIGS. 54-57 are cross-sectional views taken at various locations along the shaft 1012. Here it can be seen that the shaft 1012 may include a number of different lumens. For example, the shaft 1012 may include a first lumen 1024, a second lumen 1028, and a third lumen 1030. In this example, the proximally-extending region 1020b of the first member 1020 may extend through the first lumen 1024. The second lumen 1028 may be used for infusing a fluid such as a contrast media. The third lumen 1030 may be a guidewire lumen. In other instances, the first coating 1035a, the second coating 1035b, or both may extend through the outer surface of the shaft 1012 and into a lumen of the shaft 1012. For example, the second coating 1035b may extend into the first lumen 1024.

The materials that can be used for the various components of sphincterotomes disclosed herein may include those commonly associated with medical devices. For simplicity purposes, the following discussion makes reference to the shaft 12. However, this is not intended to limit the devices and methods described herein, as the discussion may be applied to other devices and/or components of devices disclosed herein.

The shaft 12 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), perfluoroalkoxy alkane (PFA), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-NR and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the sphincterotome 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the sphincterotome 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the sphincterotome 10 to achieve the same result.

In some embodiments, a degree of Magnetic Resonance Imaging (MRI) compatibility is imparted into the sphincterotome 10. For example, the sphincterotome 10, or portions thereof, may be made of a material that does not substantially distort the image and create substantial artifacts (e.g., gaps in the image). Certain ferromagnetic materials, for example, may not be suitable because they may create artifacts in an MRI image. The sphincterotome 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A sphincterotome, comprising:
   an elongate shaft having an outer surface and a distal end region;
   a sphincterotome wire assembly coupled to the elongate shaft, the sphincterotome wire assembly including a first member and a second member;
   wherein the first member includes a cutting region disposed along the outer surface of the elongate shaft and a first proximally-extending region;
   wherein the second member includes a non-conductive region disposed along the outer surface of the elongate shaft and a second proximally-extending region;
   a joint member disposed between and coupling the cutting region of the first member with the non-conductive region of the second member; and
   wherein the sphincterotome wire assembly is designed to shift the distal end region of the elongate shaft between a first configuration and a curved configuration.

2. The sphincterotome of claim 1, wherein the non-conductive region of the second member is non-energized when the cutting region of the first member is cutting tissue.

3. The sphincterotome of claim 1, wherein the joint member includes a housing.

4. The sphincterotome of claim 1, wherein the first member is a conductive wire.

5. The sphincterotome of claim 1, wherein the first proximally-extending region of the first member extends through a first lumen formed in the elongate shaft.

6. The sphincterotome of claim 1, wherein a distal end of the first member is anchored to the distal end region of the elongate shaft.

7. The sphincterotome of claim 1, wherein a proximal end region of the cutting region of the first member extends through an opening in the joint member.

8. The sphincterotome of claim 1, wherein a proximal end region of the cutting region of the first member is attached to the joint member.

9. The sphincterotome of claim 1, wherein the second member is a non-conductive wire.

10. The sphincterotome of claim 5, wherein the second proximally-extending region of the second member extends through a second lumen formed in the elongate shaft.

11. The sphincterotome of claim 1, wherein a distal end region of the non-conductive region of the second member is attached to the joint member.

12. The sphincterotome of claim 1, wherein the first member extends through a first port formed in the elongate shaft.

13. The sphincterotome of claim 12, wherein the second member extends through a second port formed in the elongate shaft.

14. The sphincterotome of claim 13, wherein the second port is disposed proximally of the first port.

15. A sphincterotome, comprising:
    an elongate shaft having an outer surface and a distal end region;
    a sphincterotome wire assembly coupled to the elongate shaft, the sphincterotome wire assembly including a first member and a second member;
    wherein the first member includes a cutting region disposed along the outer surface of the elongate shaft and a first proximally-extending region;
    wherein a transition between the cutting region and the first proximally-extending region is defined adjacent to a distal port formed in the elongate shaft;
    wherein the second member includes a non-conductive region disposed along the outer surface of the elongate shaft and a second proximally-extending region;
    a housing member disposed between and coupling the cutting region of the first member with the non-conductive region of the second member; and
    wherein the sphincterotome wire assembly is designed to shift the distal end region of the elongate shaft between a first configuration and a curved configuration.

16. The sphincterotome of claim 15, wherein the distal port is disposed distally of the housing member.

17. The sphincterotome of claim 15, wherein the second member extends through a second port formed in the elongate shaft.

18. A sphincterotome, comprising:
- an elongate catheter shaft having an outer surface and a distal end region;
- a sphincterotome wire assembly coupled to the elongate catheter shaft, the sphincterotome wire assembly including a first wire and a second wire;
- wherein the first wire is a conductive wire having a cutting region disposed along the outer surface of the elongate catheter shaft and a first proximally-extending region;
- wherein the second wire is a non-conductive wire having a non-conductive region disposed along the outer surface of the elongate catheter shaft and a second proximally-extending region;
- a housing member disposed between and coupling the cutting region of the first wire with the non-conductive region of the second wire; and
- wherein the sphincterotome wire assembly is designed to shift the distal end region of the elongate catheter shaft between a first configuration and a curved configuration.

19. The sphincterotome of claim 18, wherein a transition between the cutting region and the first proximally-extending region is defined adjacent to a distal port formed in the elongate catheter shaft.

20. The sphincterotome of claim 19, wherein the distal port is disposed distally of the housing member.

* * * * *